(12) United States Patent
Strange et al.

(10) Patent No.: US 11,544,520 B2
(45) Date of Patent: *Jan. 3, 2023

(54) COUNTING MECHANISM

(71) Applicant: TTP Plc, Royston (GB)

(72) Inventors: Daniel Strange, Royston (GB); Lawrence Baker, Royston (GB)

(73) Assignee: TTP Plc, Royston (GB)

( * ) Notice: Subject to any disclaimer, the term of this patent is extended or adjusted under 35 U.S.C. 154(b) by 37 days.

This patent is subject to a terminal disclaimer.

(21) Appl. No.: 17/179,485

(22) Filed: Feb. 19, 2021

(65) Prior Publication Data

US 2021/0174160 A1 Jun. 10, 2021

Related U.S. Application Data

(63) Continuation of application No. 16/310,255, filed as application No. PCT/GB2017/051724 on Jun. 14, 2017, now Pat. No. 10,929,742.

(30) Foreign Application Priority Data

Jun. 15, 2016 (GB) ..................................... 1610450

(51) Int. Cl.
    *G06M 3/02* (2006.01)
    *G06M 1/06* (2006.01)
    *A61M 15/00* (2006.01)

(52) U.S. Cl.
    CPC ........ *G06M 3/021* (2013.01); *A61M 15/0081* (2014.02); *G06M 1/064* (2013.01)

(58) Field of Classification Search
    CPC ........ G06M 3/12; G06M 3/021; G06M 1/064; G06M 3/024; G06M 3/025; G06M 3/028;
(Continued)

(56) References Cited

U.S. PATENT DOCUMENTS 1,333,061 A     3/1920   Browne
2,432,059 A  * 12/1947   Zipser ................... F16B 7/1427
                                                   403/350

(Continued)

FOREIGN PATENT DOCUMENTS

DE    10 2005 021287 A1   12/2005
WO       2004024340 A1    3/2004
(Continued)

OTHER PUBLICATIONS

International Search Report dated Oct. 17, 2017, in International Application No. PCT/GB2017/051724; Filed: Jun. 14, 2017; Applicant: The Technology Partnership PLC, now TTP PLC.
(Continued)

*Primary Examiner* — Patrick M. Buechner
(74) *Attorney, Agent, or Firm* — Erise IP, P.A.

(57) ABSTRACT

A counting mechanism (100) for a dispenser comprising: a first and a second housing part (110, 120) that are rotatable relative to each other; and a counting ring (130) disposed between the housing parts. The first housing part has a protrusion (111) which abuts the counting ring, holding a portion of the counting ring in contact with the second housing part. The relative rotation of the housing parts causes the protrusion to slide against the surface of the counting ring to drive a rolling movement of the counting ring around the circumference of the second housing part, such that a predefined rotation of the housing parts produces an incremental rotational displacement between the counting ring and second housing part to record a count. The counting mechanism provides a large gear reduction ratio in a compact form which is straightforward to manufacture and provides an accurate and reliable record of counts.

20 Claims, 17 Drawing Sheets

(58) Field of Classification Search
CPC ........ G06M 1/02; G06M 1/022; G06M 1/024;
G06M 1/04; G06M 1/041; G06M 1/045;
G06M 1/06; G06M 1/062; G06M 1/08;
G06M 1/083; G06M 1/14; G06M 1/143;
G06M 1/146; G06M 1/18; G06M 1/183;
G06M 1/186; G06M 1/22; G06M 1/24;
G06M 1/245; G06M 1/246; G06M 1/26;
A61M 5/31553; A61M 2005/3125; A61M
15/0081; A61M 15/0073; A61M 2205/27;
A61M 15/0068; A61J 7/02; G01F 11/006
See application file for complete search history.

(56) References Cited

U.S. PATENT DOCUMENTS

| | | |
|---|---|---|
| 3,171,348 A | 3/1965 | Wetzer |
| 3,419,187 A | 12/1968 | Bazarnic |
| 3,547,071 A | 12/1970 | Antrim |
| 3,984,031 A | 10/1976 | Thompson |
| 4,565,302 A | 1/1986 | Pfeiffer et al. |
| 4,616,492 A * | 10/1986 | Barfield ............... E05B 37/04 70/284 |
| 4,730,952 A * | 3/1988 | Wiley ................. B27B 5/32 403/348 |
| 5,261,548 A | 11/1993 | Barker et al. |
| 5,299,701 A | 4/1994 | Barker et al. |
| 5,313,935 A | 5/1994 | Kortenbach et al. |
| 5,638,970 A | 6/1997 | Garby et al. |
| 5,687,710 A | 11/1997 | Ambrosio et al. |
| 5,718,355 A | 2/1998 | Garby et al. |
| 5,860,387 A | 1/1999 | Giveen |
| 5,984,122 A | 11/1999 | Barker et al. |
| 5,988,496 A | 11/1999 | Bruna |
| 6,149,054 A | 11/2000 | Cirillo et al. |
| 9,022,039 B2 | 5/2015 | Hearn |
| 10,929,742 B2 * | 2/2021 | Strange ............... A61J 7/02 |
| 2005/0017020 A1 | 1/2005 | Eckert |
| 2005/0087191 A1 | 4/2005 | Morton et al. |
| 2007/0246042 A1 | 10/2007 | Purkins et al. |
| 2009/0139516 A1 | 6/2009 | Augustyn et al. |
| 2012/0111323 A1 | 5/2012 | Bacon et al. |
| 2013/0074833 A1 | 3/2013 | Sieffert et al. |
| 2014/0053838 A1 | 2/2014 | Berenshteyn et al. |
| 2017/0333635 A1 * | 11/2017 | Giambattista ..... A61M 5/31551 |
| 2022/0054775 A1 * | 2/2022 | Säll ............... G06M 3/04 |

FOREIGN PATENT DOCUMENTS

| | | | |
|---|---|---|---|
| WO | 2004/026380 A2 | 4/2004 | |
| WO | 2007/045904 A1 | 4/2007 | |
| WO | 2013110601 A1 | 8/2013 | |
| WO | WO-2013110601 A1 * | 8/2013 | ........ A61M 15/0025 |
| WO | 2013164419 A1 | 11/2013 | |
| WO | WO-2013164419 A1 * | 11/2013 | ........ A61M 15/0065 |
| WO | 2015/135083 A1 | 9/2015 | |

OTHER PUBLICATIONS

Written Opinion of the International Searching Authority dated Oct. 17, 2017, in International Application No. PCT/GB2017/051724; Filed: Jun. 14, 2017; Applicant: The Technology Partnership PLC, now TTP PLC.

European Patent Application 21209196.1 Search Report dated Mar. 28, 2022.

* cited by examiner

Section G-G

Section G-G

Section G-G

General case
(no alignment)

Rotator-counter
alignment

Rotor-stator
alignment

Lockout

COUNTING MECHANISM

RELATED APPLICATIONS

The present application is a continuation of U.S. patent application Ser. No. 16/310,255, filed 14 Dec. 2018, which is a national stage application under 35 U.S.C. § 371 of International Application No. PCT/GB2017/051724, filed 14 Jun. 2017, which claims priority to Great Britain Patent Application No. 1610450.7, filed 15 Jun. 2016. The above referenced applications are hereby incorporated by reference into the present application in their entirety.

TECHNICAL FIELD

The present invention relates to a counting mechanism, in particular a counting mechanism for a dispenser or sampler wherein the mechanism may record the number of dispensing counts or sampling counts.

BACKGROUND

Counting mechanisms and devices are well known in the art and take many different forms with the common aim of providing means to incrementally count a number of events. Such mechanisms are often incorporated into samplers to record a count of sampling events and dispensers to record a count of dispensing events. A particularly important application of counting mechanisms within dispensers is in medical devices where they can provide a record of the number of doses dispensed and remaining.

Medical devices such as inhalers, nasal sprays and injection pens are all used to deliver medication to a patient. These devices often contain multiple doses and can be used by a patient over several days or weeks. As the devices reach a near empty state, the device may emit a dose that is less than the label claim. Frequently this loss of dose is not visible to the user and therefore may result in an insufficient dose being delivered with possible implications for the effective treatment of a related condition.

It is therefore desirable for users to keep track of the number of doses that they have administered, to ensure that they are neither underdosing (leading to a lack of efficacy) nor overdosing (with potential side effects and complications). For these reasons it is desirable to include a counting mechanism in the device that indicates the number of doses remaining in the device, and that locks out to prevent the device being used once a certain number of doses have been used.

An ideal counter has a number of requirements. It must be robust and reliable and should accurately count doses regardless of how the user uses the device. It should only count when a dose has actually been delivered and it should not be possible to back track or rewind the counter and it should not lose or gain counts when dropped. The counter should also be easy to read, preferably with colouring, such that users can clearly see the number of doses remaining at a glance. Lastly, it should be low cost and easy to manufacture. Many counters in devices such as pMDIs (pressurised metered dose inhalers) contain a large number of parts in order to achieve the previous functions. This increases the cost and means such devices are more liable to malfunction through failure of one of the many components.

A large number of counters have been disclosed in the prior art, for example U.S. Pat. No. 6,651,844 discloses counters for nasal sprays and U.S. Pat. No. 9,022,039 discloses counters for simulated cigarettes. However, primarily counters have been disclosed for inhalers as several regulatory authorities have mandatory requirements for such devices.

In particular a wide range of counting mechanisms have been proposed to be used with pMDIs including mechanisms with ratchet and pawl mechanisms (US2002139812), face gears (U.S. Pat. No. 8,740,014), kick wheels (U.S. Pat. No. 8,820,318), escapement mechanisms (US2002195102) and helical tracked teeth (US20060231093). pMDI counters have a challenging set of requirements in that they must accurately keep track of the very small reciprocating movement of the actuator stem and translate this motion into a small count. As a result these counters are often very complex consisting of multiple parts and mechanisms so that they are insensitive to manufacturing tolerances.

However, there are fewer counters disclosed in the prior art that are for devices actuated using a large rotational movement, whereby the large rotational movement must be geared down into a much smaller movement of a counter wheel. U.S. Pat. No. 6,769,601 discloses a counter for a DPI (dry powder inhaler) which converts the rotation motion of a metering drum into small counts using a large geared wheel and ratchet. Although large gear reductions can be achieved with a wheel and ratchet, the counter wheel must be substantially larger than the metering drum in order to achieve the right resolution which inhibits such a mechanism being provided in a compact and user friendly device.

The counter disclosed in U.S. Pat. No. 6,149,054 comprises a spindle and tooth mechanism. An indicator flag, which is threaded onto the spindle moves upwards as the spindle is turned, indicating the count. The counter can achieve large gear reductions (60:1) and is low cost, however the resolution of the counter is limited by the length of the spindle which means that it is difficult to identify individual counts. Furthermore, the spindle requires a long, fine thread which is difficult to accurately mould with implications on the cost of manufacturing the device.

WO02006062448 discloses a counting mechanism containing an indicator strip, preferably metal, arranged around a rotatable feed wheel. The spacing of numbers on the feed wheel can be controlled so that a large number of doses can be displaced per rotation. However this requires a substantial amount of tape as there is no gear reduction, therefore having implications for the ease of manufacture and the extent to which the mechanism can be incorporated in a compact, user friendly device.

U.S. Pat. No. 8,181,645 discloses a counter for a DPI which contains two counter rings where the first (units counter ring) is driven by the indexing of the device using a large Geneva wheel and the second counter ring (tens) is driven via the first counter ring via a Geneva mechanism. The Geneva mechanism is used to convert the large continuous rotation of the counter ring into the intermittent rotation of the tens counter ring. In order to achieve the large (~120:1) gear reductions necessary to display all of the doses, the described patent has to have multiple gear reduction stages with the consequent additional parts, additional backlash and additional tolerance sensitivity.

There accordingly exists a need for a counter which is capable of large gear reductions whilst being compact such that it can be combined in a user friendly device with a small form factor. There is a further need for the counting mechanism to be formed from a minimum of constituent parts to increase the ease of manufacture and assembly while keeping associated costs down. The counter should record counts accurately and reliably whilst being robust to wear such that the counter may be used over the lifetime of the device in which it is employed. Finally there exists a need to provide means for the device to automatically lock after a certain number of counts such that, when employed in a dispenser for example, the number of doses dispensed is limited.

SUMMARY OF THE INVENTION

The present invention seeks to provide a counting mechanism which can be employed in a dispenser or sampler which solves the above described problems of prior art devices. Importantly the present invention seeks to provide a counter which can achieve large gear reductions such that a large rotational movement of the device—for example to provide the sampling or dispensing function—can be geared down to provide a small incremental movement which records a count. A further aim of the invention it to provide the large gear reductions with a minimum of complex parts in a mechanism which is robust, low cost, easy to assemble, records counts accurately and has a small form factor. The present invention further seeks to provide a lock out mechanism for a counting mechanism which can lock the count mechanism after a certain number of counts. Importantly the lock out mechanism should be reliable but formed from a minimum of parts to reduce the manufacturing and assembly costs.

According to a first aspect of the invention, there is provided a counting mechanism for a dispenser or a sampler comprising: a first housing part and a second housing part, wherein the housing parts are rotatable with respect to each other and the second housing part has a curved cross-sectional shape; a counting ring disposed between the first and second housing parts; the first housing part having a protrusion which abuts the counting ring, holding a portion of the counting ring in contact with the second housing part; wherein relative rotation of the housing parts causes the protrusion to slide against the surface of the counting ring to drive a rolling movement of the counting ring around the circumference of the second housing part; such that a predefined rotation of the housing parts produces an incremental rotational displacement between the counting ring and second housing part to record a count.

With the counting mechanism according to the present invention, a rotation of the housing parts is geared down to provide a small incremental rotation between the counting ring and one of the housing parts. In this way, a large rotation of the housing parts, for example to provide a dispensing or sampling function, is recorded by the much smaller incremental rotational displacement between the counting ring and second housing part, thus providing the required large gear reduction in a compact form.

The counting mechanism according to the present invention only requires three parts and therefore is low cost and easy to manufacture and assemble. The mechanism allows for a large number of rotations of the housing parts to be recorded whilst maintaining a small form factor for a user friendly device. The mechanism according to the present invention is furthermore highly accurate and has very little backlash.

Since the incremental movement of the counting ring is via rolling movement, there is very little wear, making the device more robust to failure of these components, prolonging the lifetime of the device. The rolling movement also provides quiet operation, increasing the user friendliness of the device.

According to a second aspect of the present invention there is provided a lock out mechanism for a counting device, the counting device comprising: a first housing part; a second housing part rotatable with respect to the first housing part; and a rotatable counting part; wherein rotation of the counting part is driven by rotation of the second housing part such that a full rotation of the second housing part produces an incremental rotation of the counting part with respect to the first housing part; the lock out mechanism comprising: a locking feature provided on each of: the counting part, the first housing part and the second housing part, the features configured to lock together when all simultaneously aligned; wherein the locking feature of the second housing part and the locking feature of the counting part are each arranged so as to align with the locking feature of the first housing part once every full rotation of the corresponding part; such that after a sufficient number of rotations of the second housing part, all three locking features are driven into alignment, triggering the lock out.

With the lock out mechanism according to the present invention, a rotatable three part counting mechanism (wherein one of the parts is driven by rotation of the others) may be prevented from further rotation once a predefined number of counts are recorded. The lock out mechanism utilises the fact that the three parts only align once during the lifetime of the device and therefore simultaneous alignment may be used to initialise lockout. The simplicity of the mechanism means it is straightforward and low cost to manufacture and the possibility of failure is reduced. The possibility of introducing a sprung feature which is driven orthogonally to the direction of rotation means the parts are tightly locked and cannot be easily overcome by applying a force to rotate the housing parts.

BRIEF DESCRIPTION OF THE DRAWINGS

Embodiments of the invention will now be described, by way of example only, with reference to the accompanying drawings, in which.

DETAILED DESCRIPTION

Figure 1A:
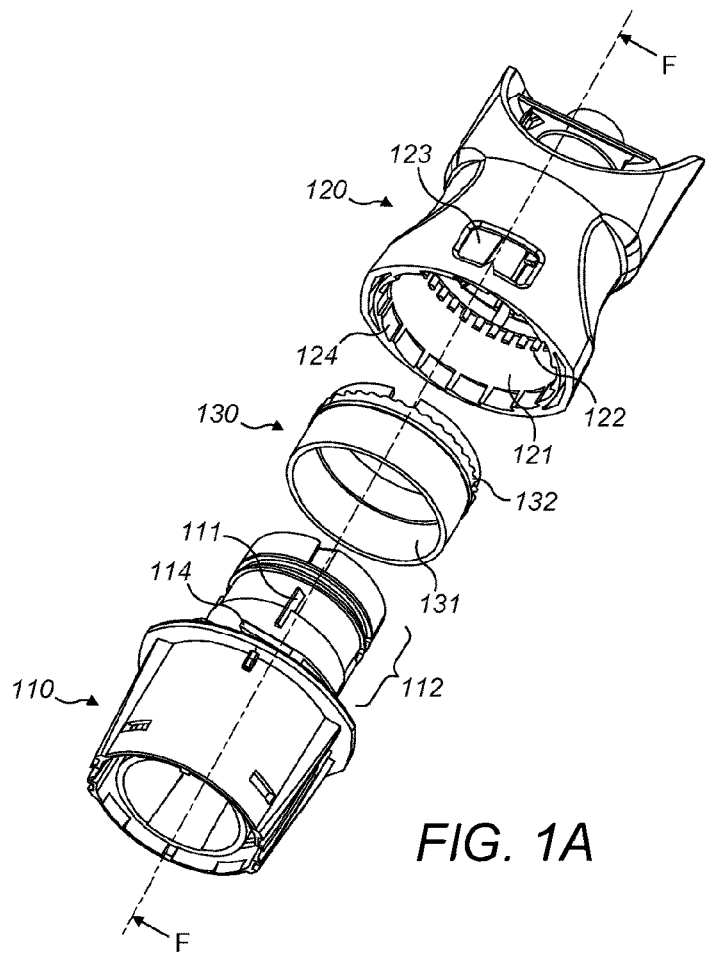
FIGS. 1A and 1B schematically illustrate an exploded view and a cross section of a first example of a counting mechanism according to the present invention.
Figure 1B:
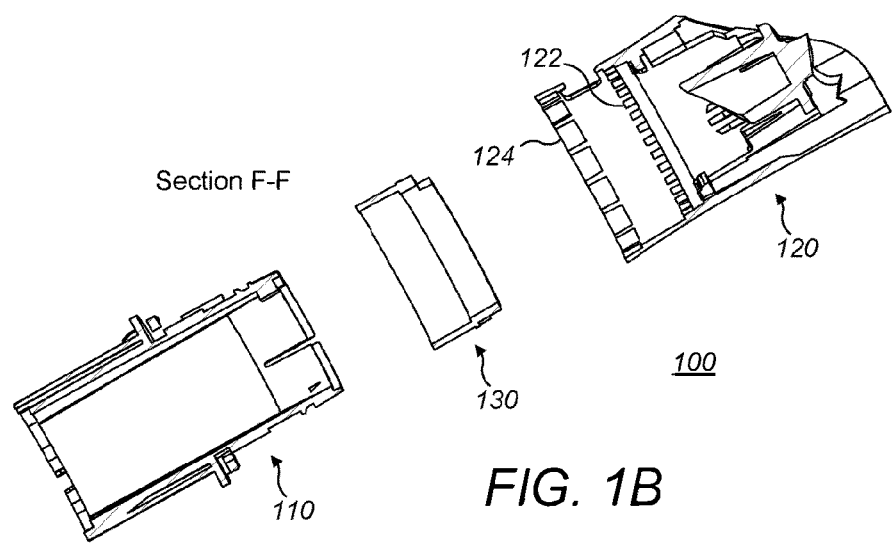

FIGS. 1A and 1B schematically illustrate a counting mechanism 100 according to the present invention. The counting mechanism 100 comprises a first housing part 110 and a second housing part 120. The second housing part 120 has a curved cross-sectional shape and is rotatable relative to the first housing part 110. The counting mechanism 100 further comprises a counting ring 130 which is positioned between the first 110 and second 120 housing parts. The first housing part 110 has a protrusion 111, shown in the exploded view of FIG. 1A which is positioned so as to abut the counting ring 130 when the mechanism 100 is assembled.

When assembled the protrusion acts so as to hold the counting ring 130 against the second housing part 120. When the housing parts 110, 120 are rotated the protrusion slides against the surface 131 of the counting ring 130 which drives a rolling movement of the counting ring 130 around the circumference of an opposing curved surface of the second housing part 120. In this way, a predefined rotation of the housing parts 110, 120 produces an incremental rotational displacement between the counting ring 130 and second housing part 120. The number of incremental rotational displacements between the counting ring 130 and second housing part 120 therefore provides a record of the number of predefined rotations of the housing parts.

Cycloidal Mechanism

Figure 2A:
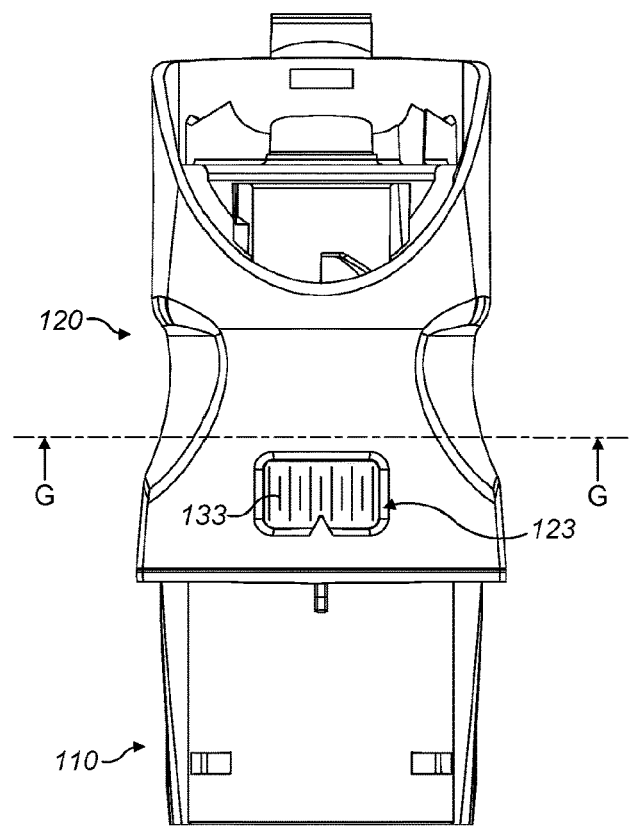
FIGS. 2A and 2B schematically illustrate a front view and a cross section of the first example of a counting mechanism according to the present invention.

In the example of FIG. 1, the first housing part, the second housing part and the counting ring each have a substantially cylindrical shape. The counting ring 130 has a radius such that, when the device is assembled by bringing the parts together along the axial direction F-F, the counting ring 130 fits over a portion 112 of the first housing part and lies within the second housing part 120. The second housing part 120 substantially encloses the counting ring 130 and at least a portion 112 of the first housing part, as illustrated in FIG. 2A.

Figure 2B:
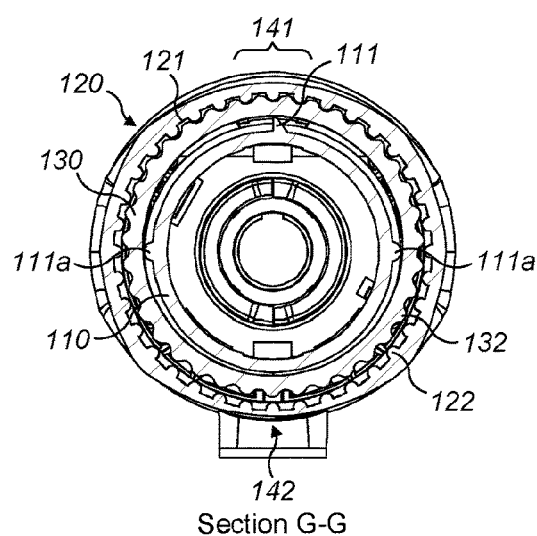

The interaction between the housing parts 110, 120 and the counting ring is best illustrated by the cross-section G-G shown in FIG. 2B. In this example, once assembled, the housing parts 110 and 120 are substantially coaxial, with a portion of the first housing part 110 lying within the second housing part 120 such that they are substantially concentric as shown in FIG. 2B. The counting ring 130 is positioned between the overlapping portions of the first and second housing parts, and is displaced off-axis by the contact of the radially extending protrusion 111 of the first housing part 110. Therefore, when assembled, the housing parts 110, 120 share a common axis of rotation, shown as F-F in FIG. 1A, and the counting ring 130 is eccentrically positioned, displaced from this axis. As shown in FIG. 2B the protrusion 111 extends outwards radially from the first housing part 110 to abut the inner surface of the counting ring 130 and hold a portion of the outer surface of the counting ring 130 in contact with the inner surface of the second housing part 120. In this example the counting ring 130 is therefore eccentrically positioned with respect to the housing parts 110, 120. The diameter of the counting ring is such that, when assembled with a portion of the counting ring 130 in contact with the second housing part 120 at a first position 141 adjacent to the protrusion 111, the counting ring is separated from inner surface of the second housing part 120 at a second position 142 corresponding to the opposite side of the first housing part to the protrusion 111.

The first housing part 110 may have one or more additional radial protrusions 111a circumferentially separated from the first 111 by 90 degrees. The additional protrusions 111a are smaller than the first 111, such that they do not extend far enough radially to produce contact between the counting ring 130 and second housing part 120. Instead, the protrusions 111a may help in adding further stability to the counting ring, aiding in holding it in the correct eccentric position shown in FIG. 2B.

When the first housing part 110 is rotated about axis F-F with respect to the second housing part 120, the protrusion 111 slides against the inner surface of the counting ring as the first housing part rotates within the counting ring 130. The portion 141 of the counting ring held in contact with the inner surface 121 of the second housing part 120 therefore moves with the protrusion, such that the counting ring rolls around the inner circumference of the second, outer housing part 120. Since the circumference of the outer surface of the counting ring 130 is smaller than the circumference of the inner surface 121 of the second housing part 120, a full clockwise rotation of the first housing part will produce an incremental anticlockwise displacement of the counting ring 130 relative to the second housing part 120, provided the counting ring 130 rolls against the inner surface of the second housing part without slipping. The counting ring 130 and opposing surface 121 of the second housing part 120 therefore provide the gears, configured to produce the reduction in rotational motion of the counting ring 130 relative to the housing parts.

In order to facilitate the rolling movement of the eccentrically mounted counting ring 130 around the circumference of the inner surface 121 of the second housing part and to substantially prevent slipping, the mechanism may further preferably comprise two opposing arrays of gear teeth 122, 132. As shown in FIG. 2B an array of teeth 132,122 is provided both around the circumference of the outer surface of the counting ring 130 and the opposing inner surface of the second housing part 120. The eccentric displacement of the counting ring 130 by the protrusion 111 therefore causes the opposing gear teeth to mesh at the contacting portion 141 of the counting ring 130 and second housing part 120. The diameter of the counting ring 130 may be such that there is a separation between the opposing gear teeth at a position 142 on the side of the mechanism opposite that of the protrusion 111. As the first housing part 110 rotates, the position of the meshed gear teeth moves around the housing, driven by the sliding contact of the protrusion on the inner surface of the counting ring 130. The rolling movement of the counting ring 130 against the surface of the second housing part is therefore provided by a sequential interlocking of the gear teeth around the inner circumference of the second housing part 120.

The interlocking gear teeth 122, 132 prevent the counting ring 130 from slipping relative to the surface 121 of the second housing part 120 since the position of the counting ring is restricted to the positions in which the teeth mesh. Relatedly, the gear teeth 122, 132 also define the rotational displacement between the counting ring 130 and second housing part 120 provided by a rotation of the first housing part 110 relative to the second housing part 120. For example, if the difference in circumferences of the inner surface of the second housing part 120 and the outer surface of the counting ring 130 is accounted for by providing one extra tooth on the array of gear teeth 122 on the second housing part, a full rotation of the housing parts will produce a rotational displacement equivalent to the separation between consecutive teeth. This can be pictured from the diagram of FIG. 2B where a full clockwise rotation of the first housing part 110 relative to the second housing part 120 will cause the counting ring 130 to move anticlockwise relative to the second housing part 120 by a distance corresponding to one tooth.

The cycloidal gearing system provided by the example of present invention illustrated in FIGS. 1 and 2 allows for a very high gearing ratio to be provided in a compact form since, unlike conventional gearing mechanisms, the highest gearing ratios are provided when the two gears have a similar number of teeth rather than greatly differing numbers of teeth. The components can therefore be of a similar size and be integrated in a compact form. The gearing reduction ratio provided by this type of gearing mechanism used in this example of the present invention may be calculated by $$\text{Reduction Ratio} = \frac{\text{Inner teeth} - \text{Outer teeth}}{\text{Inner teeth}}$$

Therefore, when applied in a dispenser, in order to provide a 35:1 gearing ratio the inner gear could have 35 teeth and the outer 36.

For a toothed cycloidal gear, the maximum single-stage gear reduction which can be achieved is therefore equal to the number of inner teeth which can be fitted on the part. The number of teeth which can fit along a given length is limited by part tolerances and the potential for clashes in the mechanism.

Furthermore, the rotational motion of the counting ring is continuous and can therefore be used to measure fractions of a revolution—this is useful because a dispensing or sampling device may be designed to dispense multiple doses per revolution. For example, a counter with a 35:1 gearing could be used to count 70 doses, if a single dose was dispensed every 180° turn of the first housing, relative to the second housing.

Figures 3A, 3B:
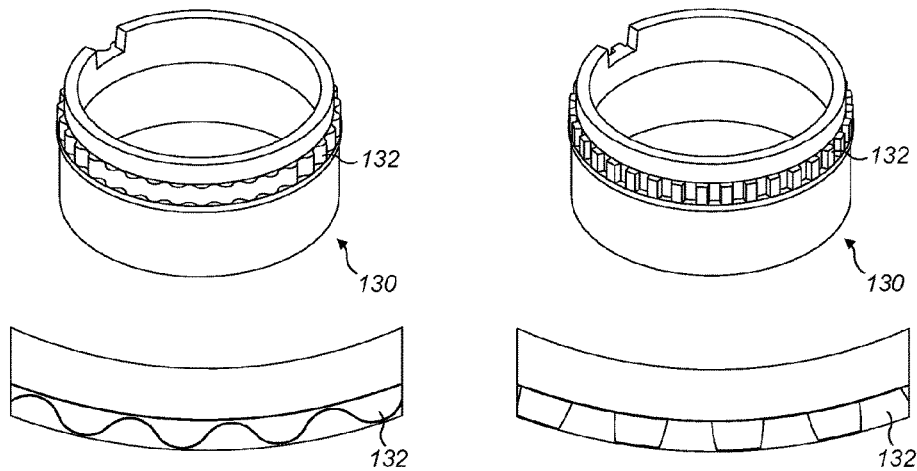
FIGS. 3A to 3D schematically illustrate various alternative forms that the optional gear teeth of the counting mechanism may take.
Figures 3C, 3D:
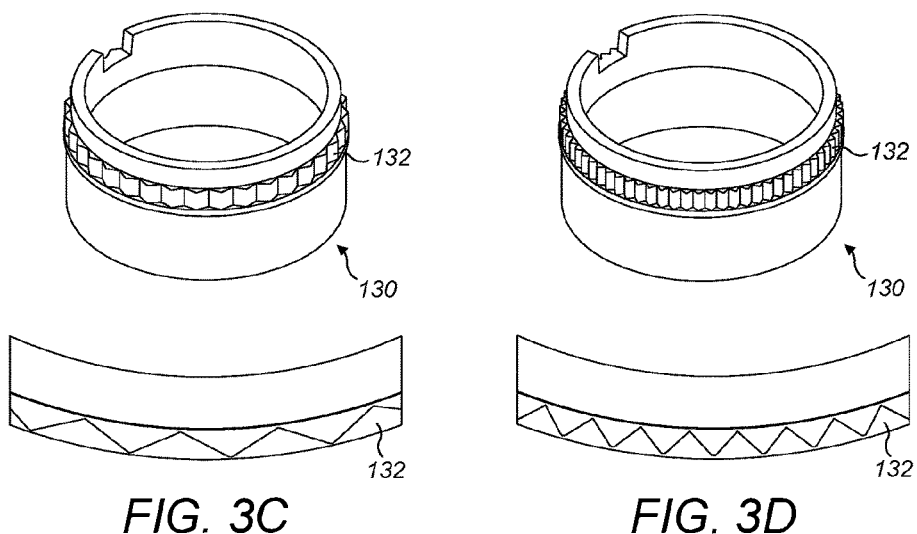

The example of FIG. 2 uses a cycloidal tooth profile, as shown enlarged in FIG. 3A. A cycloidal tooth profile provides a strong connection between the counting ring and second housing part. This shaped profile also reduces interference in the non-meshed portions. Since the profile rolls rather than slides over the opposing teeth and the teeth have a convex flank, wear is minimised and operation is quiet. The high strength and low wearing make cycloidal teeth preferable for use in the current invention, however several other tooth shapes may equally be used. FIG. 3B illustrates a further option in the form of an involute tooth profile. This tooth profile shape is formed of a single curve and a flat and therefore is economic to machine. Involute gear teeth also provide a constant pressure angle throughout rotation and rotate at a constant velocity irrespective of the gear centring. FIGS. 3C and 3D show a 35 saw-tooth counting ring and a 70 saw-tooth counting ring respectively. Since the saw-tooth shape has steeper tapering towards the end of the tooth, the probability of clashing is lowered. In a preferred embodiment cycloidal teeth are used due to the low wear, but where high gearing ratios are preferred (for instance on a 70:1 counter) a saw-tooth may be preferable, because clashes become more likely as the number of teeth increases and the steeper tapering of this shape helps to mitigate this effect.

Figure 4:
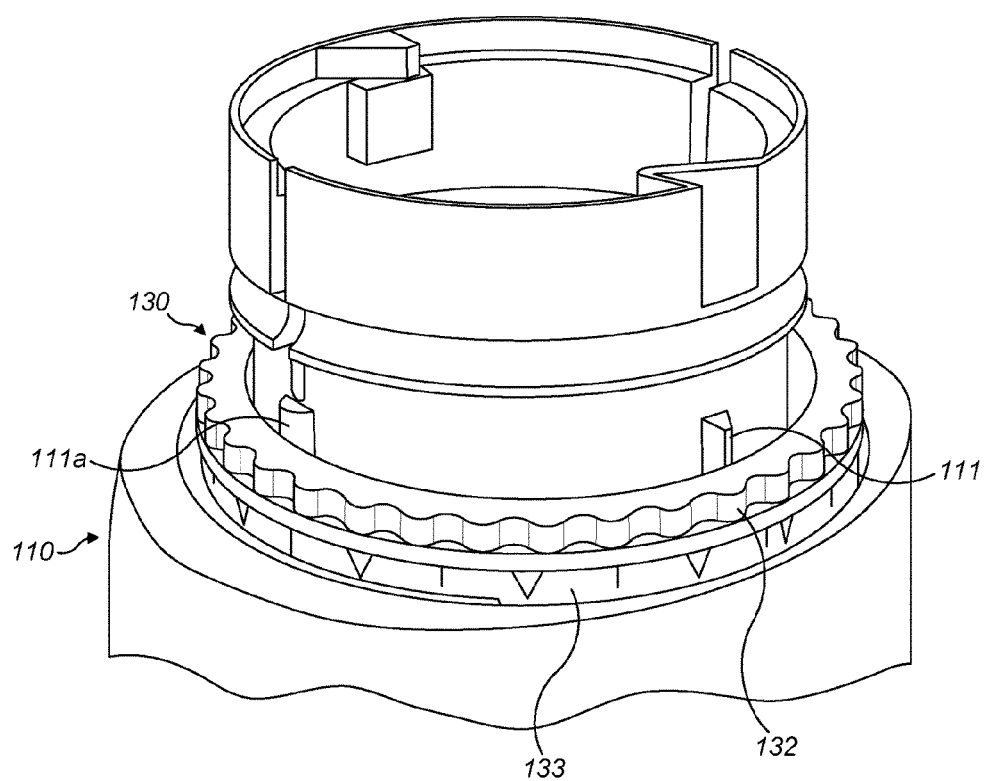
FIG. 4 schematically illustrates the assembly of the first housing part and counting ring of a counting mechanism according to the present invention.

As described above, since rotation of the housing parts causes a much slower rotation of the counting ring 130 relative to the second housing part 120, the rotational displacement of the counting ring 130 may provide a count of the number of rotations of the housing parts (and therefore a count of the number of doses dispensed in the case of a dispenser or sampling events in the case of a sampler). In order to communicate the count information to a user, a scale 133 may be provided on the mechanism to provide a visual indication of the rotational displacement between the counting ring 130 and second housing part 120. FIG. 4 is an illustration of the first housing part 110 and counting ring 130 which shows a possible scale 133 provided on the counting ring 130. This may be created by printing or the application of a label for example with gradations and colours providing a visual indication of the number of doses remaining. For instance, amber may be used to make the user aware that they should order another device and red to indicate that there is less than one week of dose remaining. Additionally numbers may be added to provide an exact number of doses remaining. The scale 133 may be combined with a window 123 on the second housing part 120 such that only a portion of the scale 133, corresponding to the current number of rotations, is visible to the user. Since this rotational displacement between the second housing part and counting ring provides the count, the scale features—the scale 133 and window 123 in this case—should be provided on these components to together provide a record of counts.

To ensure the mechanism cannot be driven in the reverse direction—corresponding to an anti-clockwise rotation of the first housing part 110 in FIG. 2B—the mechanism may additionally include a ratchet feature 124 and a pawl feature 114. In the example of FIG. 1A the ratchet 124 is provided around the internal surface of the second housing part 120 and the pawl 114 is provided on the first housing part 110.

Figure 5C:
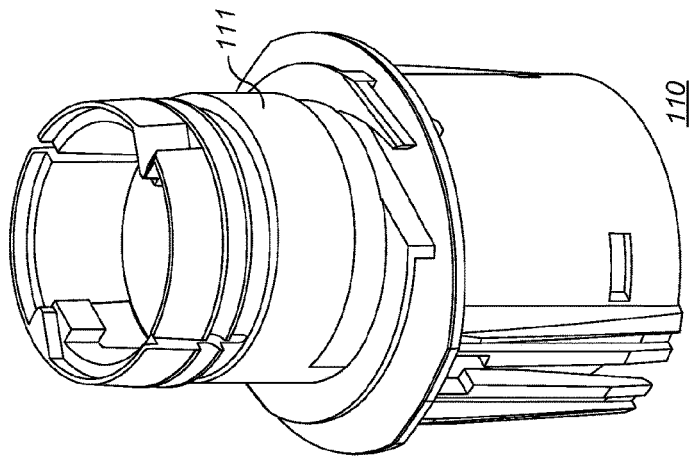
FIGS. 5A to 5E schematically illustrate various alternative forms that the protrusion of the first housing part may take.
Figure 5B:
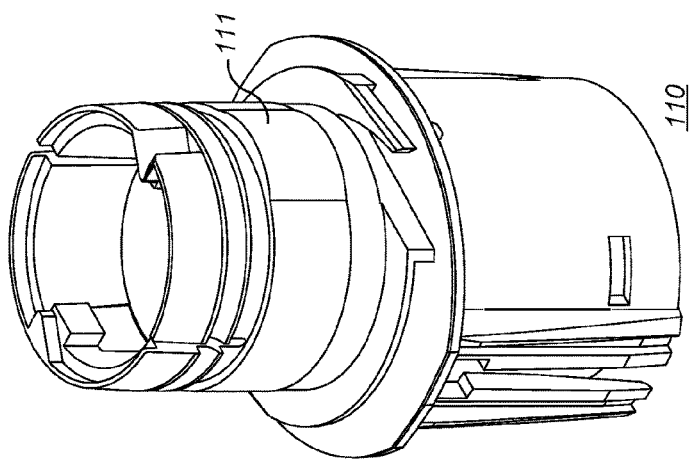
Figure 5A:
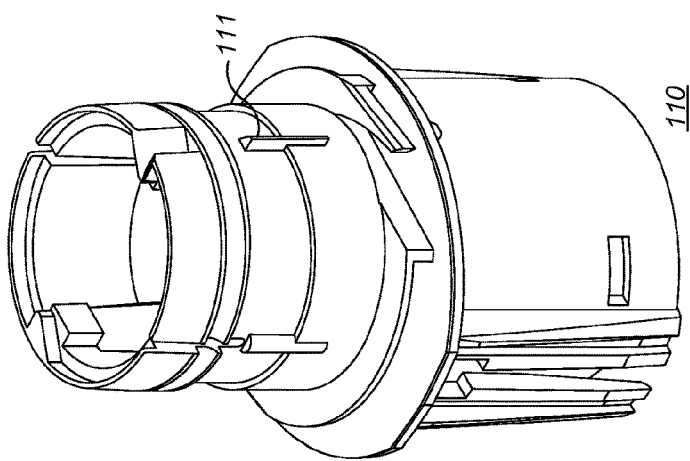

In the exemplary mechanism of FIGS. 1 to 4, the protrusion 111 is a wedge feature which protrudes radially from the first housing part in order to provide the eccentric displacement of the counting ring and required contact with the second housing part. This may additionally be supplemented by smaller wedge or semi-circular protrusions 111*a* circumferentially offset from the first—in this example by 90°. Three or more contact points on the inner surface 131 of the counting ring 130 work together to hold the counting ring in the correct eccentric position such that the opposing teeth 122, 132 of the counting ring 130 and second housing part 120 mesh at the contact point 141 adjacent to the main protrusion 111. There are several alternative forms the radial protrusion 111 may take, as illustrated in FIGS. 5A to 5E. In place of the small wedge features shown in FIG. 5A, the radial protrusion 111 may take the form of a pear shaped cam formed on the outer surface of the first housing part as illustrated in FIG. 5B. Alternatively, the radial protrusion may be provided by the body of the first housing part having a cross-sectional shape defined by an eccentrically centred circle, as illustrated in FIG. 5C. In this case the eccentricity is provided by the non-uniformity in the cross-section of the housing part.

Figure 5D:
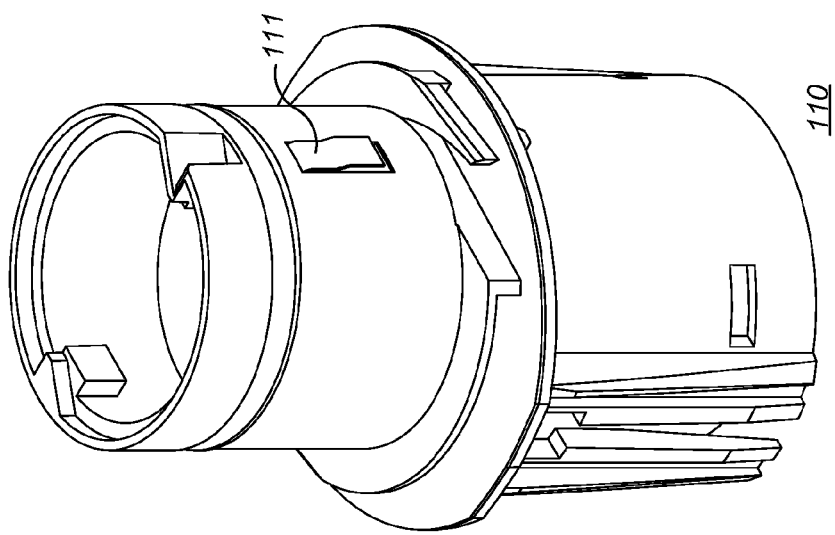
Figure 5E:
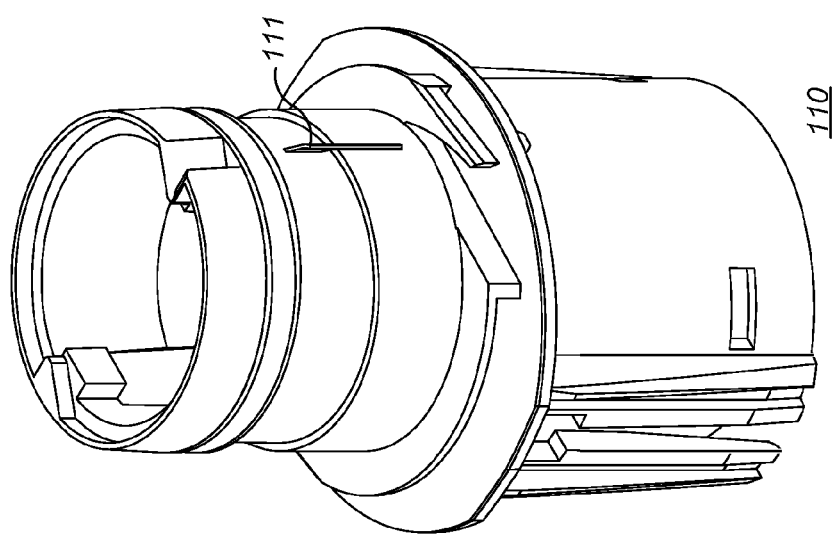

Alternatively to the above described rigid features, the protrusion may alternatively take the form of a sprung feature. FIGS. 5D and 5E show a lower housing part 110 in which the protrusion 111 is provided by a moulded spring and a leaf spring respectively. The addition of a spring feature increases the complexity of manufacture compared to the above integrally formed examples, however a sprung feature ensures a positive engagement force at all times and helps to alleviate any tolerance stacks within the mechanism. This spring feature could be formed in moulded plastic on one of the housing or counting parts, or it could be a separate part altogether. Although having a separate spring part would complicate assembly and add cost, it allows metal springs to be used, which have desirable material properties for springs, such as energy stored per unit volume.

In the above described examples, the counting ring 130 is provided by a rigid part, for example manufactured from rigid plastic. This is so that the force applied by the protrusion 111 acts to displace the counting ring 130 off-axis without it deforming or substantially changing shape in any way. However, rather than comprising a rigid part, the counting ring 130 could alternatively be a flexible belt. Example materials for this belt could be an elastomer, for instance: silicone, EPDM, TPE, TPU or Viton; a polymer, typically with low modulus, such as a polyolefin, or a reticulated or very thin section of an engineering polymer or metal. The flexible belt may be advantageous because it largely eliminates issues with teeth 122, 132 clashing. The gearing ratio achievable is limited by the number of teeth on the counting ring and second housing part, and the number of teeth (for a given volume) is limited by how small those teeth can be made. The minimum size of teeth is dictated by achievable tolerances—gears where teeth are out of tolerance will clash and jam. If a flexible material is used for the counting ring 130, then it is unable to support compressive load and it will simply deform instead. Because compressive loads cannot be supported, the counter cannot jam, and this decreases the minimum viable tooth size for the mechanism, which means many teeth can be fitted within a small volume. However, the primary disadvantage of a belt driven system is that the position of the unmeshed portion of the belt is unknown—this makes a belt unsuitable for communicating count information to the user. This issue could also be corrected by using additional features or parts, such as constructing a counting ring 130 with living hinges between a driven belt and a more rigid count indicator. There is a continuum between a substantially rigid counter which maintains the shape of the unmeshed section, but suffers from clashing and a flexible counter which does not hold its shape but does not suffer from clashing. A semi-rigid polymer counter may offer a good compromise between accuracy and sensitivity to clashing, for a specific counter.

Additionally, the counting mechanism may include features on the counting ring 130 or housing parts 110, 120 which trigger functions at certain points during the lifetime of the device. For example once a feature on the incrementally rotating counting ring 130 has reached a certain rotational displacement a signal or light may be displayed to a user or, if employed in a dispenser, the volume of dose dispensed may change.

An important example of a function triggered in this way may be lockout of the device triggered at the end of the lifetime (as indicated by a certain rotational displacement of the counting ring). For example the device may have an end of life lockout which triggers after 70 doses. This may be achieved by having a slot on the counter, a slot on the lower housing and a sprung member on the upper housing, which only align once 70 doses (for example) have been dispensed. The sprung member is driven into the slots orthogonally to the direction of rotation of the housings. This effectively locks the upper housing, lower housing and counting ring together, preventing the user from dispensing more doses.

The lockout mechanism is described in more detail below.

The counting functionality is not dependant solely on a lockout or a count indication to the user; it may also be used for collecting data to send to a third party.

Multi-Stage Mechanism

Although the examples described above use a single counting ring 130 to record counts, to achieve very large gearing ratios in a compact size, a multi-stage mechanism can be used. In terms of gearing ratio, adding further stages scales geometrically, whereas adding more teeth scales additively, so eventually it will always be preferable to add further stages, rather than add more teeth. An advantage to the mechanism according to this invention is that a second stage can be added with only a single extra part. Further stages after the second can also be added with only a single extra part each.

A two-stage embodiment of this counter which can be used to achieve very large reduction ratios is to have a second counting ring, which is largely the same as the upper housing, except it has one more (or less) internal tooth. In this example, every full rotation of the first housing part relative to the second housing part offsets the first counting ring from the upper housing by one tooth (1st stage) and every full rotation of the counting ring offsets the second counting ring and the outer housing off by one tooth (2nd stage). For the above described mechanism this would give a gearing ratio for the first stage of 35:1 and a gearing ratio for the second stage of 36:1, giving a total gearing ratio of 1260:1 in a counter which only requires four parts, two of which are formed by housing parts 110, 120.

Further stages can be added by placing a protrusion on the free surface of the second stage and using this to drive a further cycloidal gear. Since the second stage forms the driving component (first housing part equivalent) and the fixed reference (upper housing) can be shared between all stages—a third stage is comprised of a second counting ring and a fourth stage can be added in the same manner as the second. This can be repeated such that a mechanism with n stages only requires n+2 parts (or n extra parts once discounting the housings)

A multi-stage mechanism may be particularly advantageous for applications which need a very large gearing ratio in a small diameter. The diameter of the geared parts is essentially proportional to the number of teeth they contain, so larger gearing ratios require larger diameters. By instead stacking gears, a mechanism could maintain a small diameter at the cost vertical space. This form factor is particularly useful for long thin products, such as parenteral drug delivery devices or e-cigarettes.

Inverse Cycloidal Mechanism

FIGS. 6A to 6D show a further example of a counting mechanism according to the present invention. This example is similar to the cycloidal mechanism examples described above and employs the same operating principles but the housing parts 110, 120 have the "inverse" functionality. In particular, the upper, outer housing part acts as the first housing part 110 which drives the counting ring 130 and the inner, lower housing part acts as the second housing part 120 against which the incremental rotation of the counting ring 130 is measured.

Figure 6A:
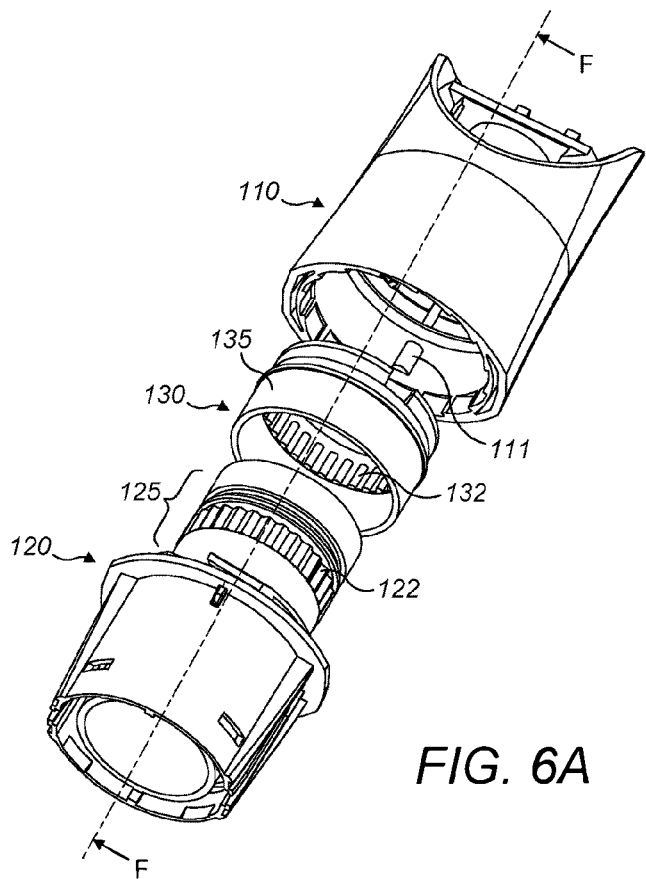
FIGS. 6A and 6B schematically illustrate an exploded view and a cross section of a second example of a counting mechanism according to the present invention.
Figure 6B:
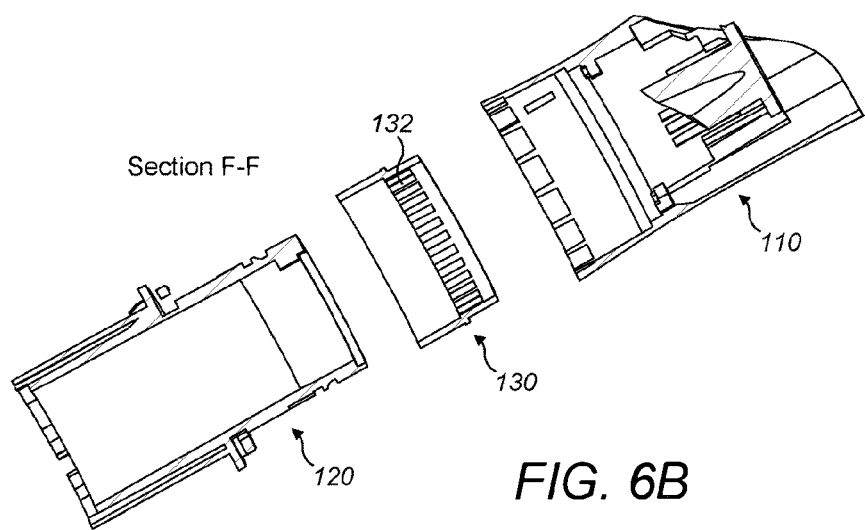
Figure 6C:
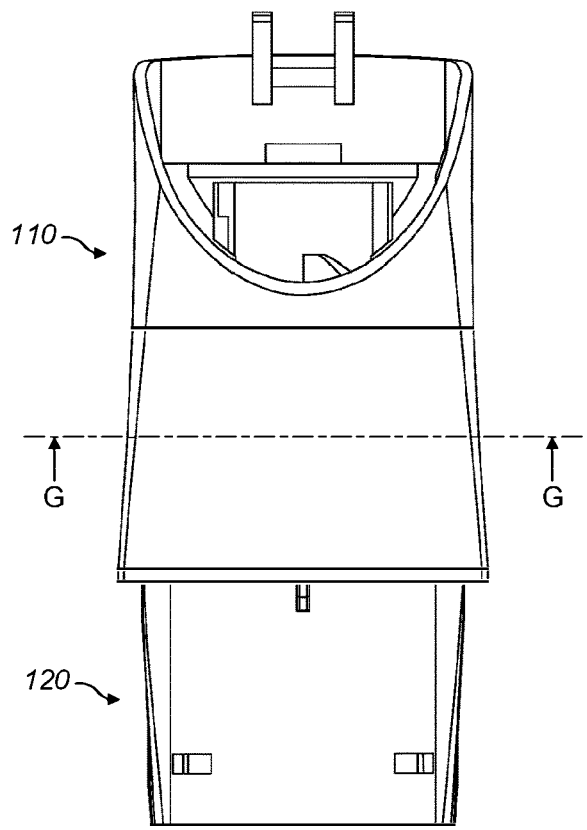
FIGS. 6C and 6D schematically illustrate a front view and a cross section of the second example of a counting mechanism according to the present invention.
Figure 6D:
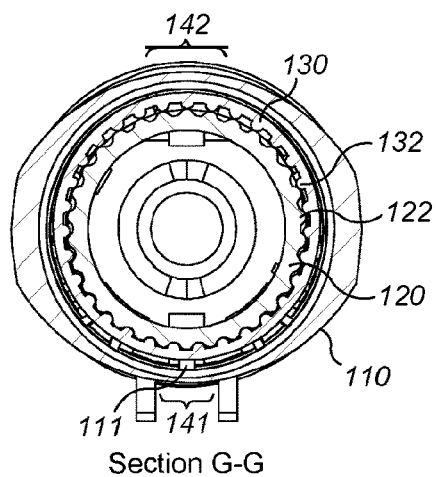

In this example, the counting ring 130 lies around the second (lower) housing part 120 and within the first (upper) housing part. The radial protrusion 111 extends inwardly from the smooth inner surface of the first (upper) housing part to contact the outer surface of the counting ring 130. The contact of the protrusion 111 on the counting ring shifts the counting ring off-axis such that the inner surface 131 is held in contact with the outer-facing surface 125 of the second (lower) housing part 120. The counting ring 130 of this example has a circumferential array of teeth 132 running around the inside surface of the counting ring 130. The second housing part has an opposing array of teeth 122 which run around the circumference of the outer facing surface of the portion 125 of the second housing part 120 on which the counting ring 130 lies. The contact of the radial protrusion 111 with the counting ring 130 therefore causes the opposing teeth 122, 132 to mesh at a position 141 adjacent to the protrusion 111, as shown in FIG. 6D.

In this example, utilising the inverse operation to the cycloidal arrangement described above, the operation of the device is best understood by considering the second (lower) housing part 120 as fixed, with the first (upper) housing part rotating. As the first housing part 110 is rotated with respect to the second housing part 120, the protrusion 111 slides against the outer surface 135 of the counting ring 130, causing the inner surface of the counting ring 130 to roll against the outer surface of the second housing part 120. The meshed contact portion 141, shown in FIG. 6D, therefore propagates around the interface of the counting ring 130 and second housing part 120, the rolling movement facilitated by a sequential interlocking of the opposing gear teeth 122, 132.

In this inverse arrangement, the counting ring 130 has more teeth than the second housing part 120 such that, after a full rotation of the first housing part 110 relative to the second housing part 120, the counting ring 130 will have moved forward relative to the second housing part 120 by a rotational displacement corresponding to the difference in number of teeth. The number of incremental rotational displacements between the counting ring 130 and second housing part 120 (as measured from a known starting point) therefore provides a record of the number of rotations of the housing parts 110, 120.

Since in this inverse arrangement the counting motion is happening between the lower (second) housing 120 and counting ring 130, it is preferable to have any counting scale 133 or indication between these two parts. The counting indication can take place between the upper housing and the counting ring, but then it is preferable to cover the scale during the motion (and uncover after each full rotation for example) otherwise the user might become confused as to how many counts were shown.

A disadvantage of the inverse mechanism when compared to the above described example is that because the teeth are formed at a smaller radius there is less room for teeth, which limits the maximum gear reduction available.

Friction-Based Mechanism

The central function of the gear teeth 122, 132 in the above embodiments is to ensure that the movement of the counting ring 130 with the second housing part 120 is solely via a rolling contact and that there is no slipping of the surfaces against each other. Since the count of rotations of the housing parts 110, 120 is provided by the fixed ratio between the amount of rotation of the housing parts and the induced incremental displacement between the counting ring and second housing part, any slip would disrupt this ratio (by producing more than just the incremental displacement) and therefore result in an inaccurate record of counts. However the non-slip condition can equally be provided by alternative mechanisms other than the opposing arrays of teeth, as long as this condition can be achieved to an extent necessary to provide a required accuracy.

Figure 7A:
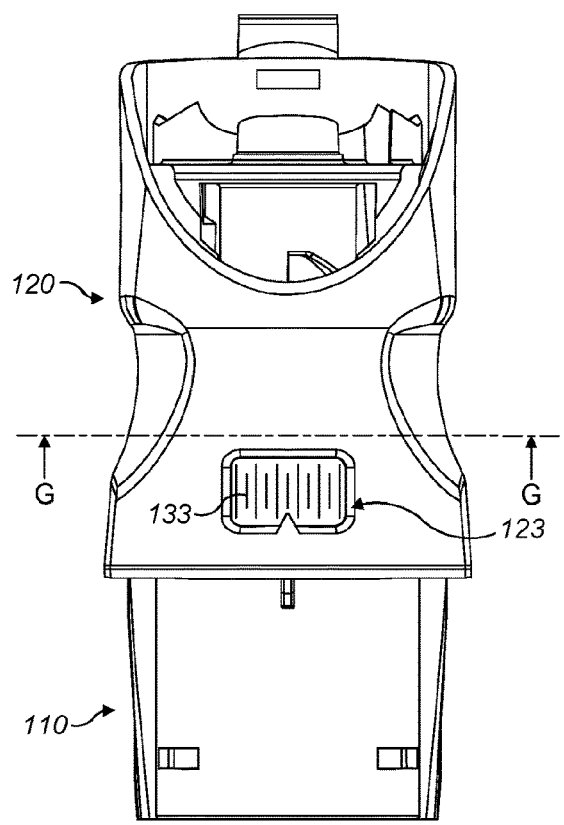
FIGS. 7A and 7B schematically illustrate a front view and a cross section of the third example of a counting mechanism according to the present invention.
Figure 7B:
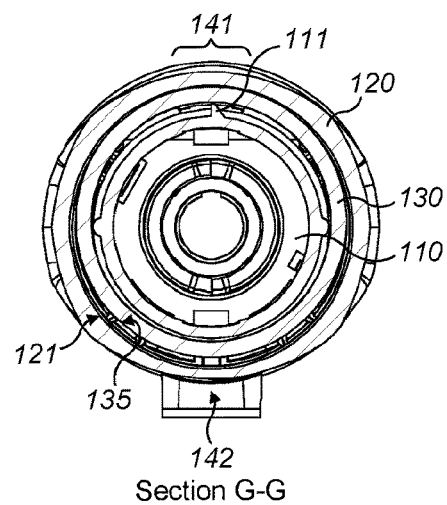

FIGS. 7A and 7B illustrate one such mechanism which uses high friction surfaces 121, 135 rather than teeth to achieve the required non-slip condition. In this example, the arrangement of the housing parts 110, 120 and counting ring 130 are identical to that described with reference to FIGS. 1 to 4. However instead of circumferential arrays of teeth being provided around the opposing surfaces of the counting ring 130 and second housing part 120, these surfaces are configured to provide a high friction contact, sufficient to provide the no slip condition.

In order to minimise slippage it is desirable to maximise both the coefficient of friction and reaction force between the counting ring 130 and second housing part 120. Reaction force can be maximised by using a sprung part (as detailed previously), or by having materials which elastically deform combined with an interference fit. Friction can be maximised by surface treatment, texturing or using similar, high friction materials, such as silicone or TPE. The use of TPE could be particularly advantageous, because it could be over moulded or moulded as part of a two shot process—rather than requiring a separate assembly step.

An advantage of this mechanism is that removing the teeth completely eliminates the possibility of clashes and ties the theoretical maximum gear ratio to the tolerances on the perimeter of the counting ring 130 and the second housing part 120. As long as the non-slip condition can be maintained and the user is able to read the scale with sufficient precision given the small incremental movements, extremely high gearing ratios are achievable. For example a counting ring with an outer perimeter of 100 mm and a second housing part 120 with an inner perimeter of 100.25 mm would give a gearing ratio of 400:1 in a single stage.

The disadvantages of this mechanism include the possibility that the counting ring may be more prone to slipping with only friction acting rather than a mechanical reaction force. Furthermore, since the gearing ratio is determined by a continuous variable (ratio of perimeters) rather than a discrete one (the ratio of teeth) it is very tolerance sensitive. By way of illustration, if in the example above there was a ±0.1 mm tolerance on the perimeter of each of the parts, then if the parts were within specification the gearing ratio could be anywhere between 222:1 and 2002:1.

Harmonic Gear Mechanism

Figure 8A:
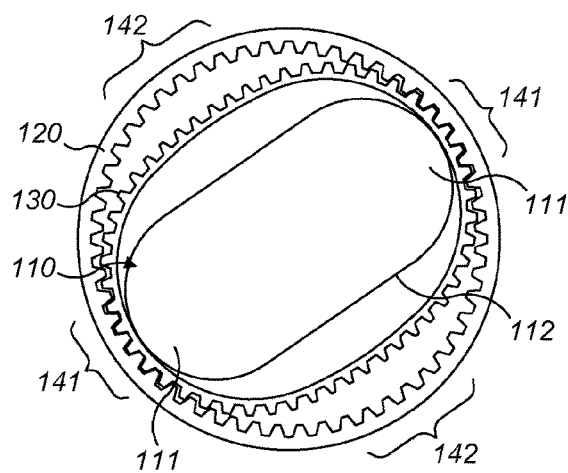
FIGS. 8A to 8F schematically illustrate a cross sectional view of a fourth example of a counting mechanism according to the present invention and various alternatives for the constituent parts.

A further example of a counting mechanism according to the present invention is illustrated in FIG. 8A. Again, the principle of operation of this example is very similar to that described with reference to FIGS. 1 to 4. However in this case, rather than being mounted eccentrically, the counting ring 130 is flexible and is deformed to contact the inner surface of the second housing part at certain points due to the shape of the first housing part around which it is positioned.

The arrangement of the housing parts 110, 120 and counting ring 130 is similar to that shown in FIG. 1A, with the counting ring 130 positioned around a portion 112 of the first housing part 110 and lying within the second housing part 120. However in this example, the radial protrusions are provided by the cross-sectional shape of the portion 112 of the first housing part 110 around which the counting ring 130 is positioned. For example, in the example of FIG. 8A the cross section of the portion 112 of the first housing part has an elliptical or rounded rectangular cross-section wherein the ends of the elongate axis of the ellipse provide the radial protrusions 111. Since the counting ring 130 is flexible and the length of the elongate axis of the elliptical cross-section is greater than the diameter of the relaxed counting ring 130, the counting ring must deform when placed around the first housing part 110. The cross-sectional shape of the first housing part portion 112 is appropriately sized such that the deformation of the counting ring 130 causes the counting ring 130 to contact the inner surface of the second housing part 120 at positions 141 corresponding to the protrusions 111.

As with previous examples, two opposing circumferential arrays of gear teeth may be provided around the counting ring 130 and second housing part 120 with a differing number of teeth provided on each component. The contact between the counting ring 130 and second housing part 120, imparted by the first housing part protrusions 111, therefore results in the meshing of the opposing gear teeth at the contacted positions 141.

When the first housing part 110 is rotated relative to the second housing part 120, the rotation of the elliptical cross-section of the first housing part portion within the counting ring 130 causes the radial deformation of the counting ring 130 to propagate around the circumference of the counting ring 130. The counting ring 130 therefore rolls against the opposing surface of the second housing part and proceeds via a sequential interlocking of teeth. A full rotation of the first housing part relative to the second housing part therefore produces the required incremental rotational displacement between the counting ring and second housing part corresponding to the difference in number of teeth.

A difference in the configuration of this example is that the first housing part provides at least two contact points 141 between the counting ring 130 and second housing part 120. The example of FIG. 8A has two in-phase contact regions in which the teeth are meshed with two regions 142 which are 90 degrees offset from these contact points 141. Because there are two points of contact 141, difference in the number of teeth between the counting ring 130 and second housing part must be even—which halves the achievable gearing ratio. An advantage of this harmonic gear example is that the two points of contact allow for greater load transmission before yield, although generally in counting applications the loads transmitted are not significant.

Figure 8B:
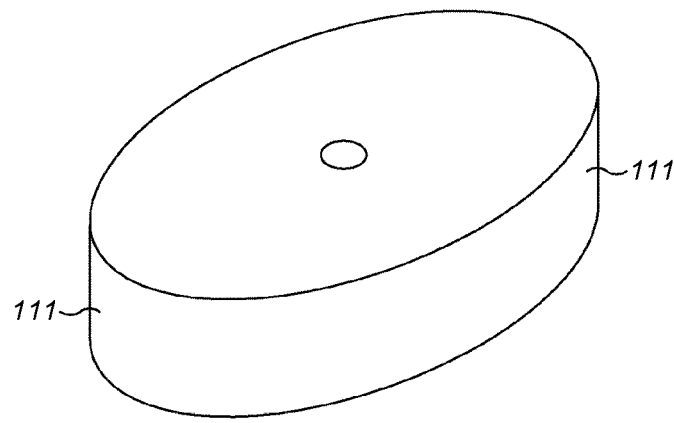
Figure 8C:
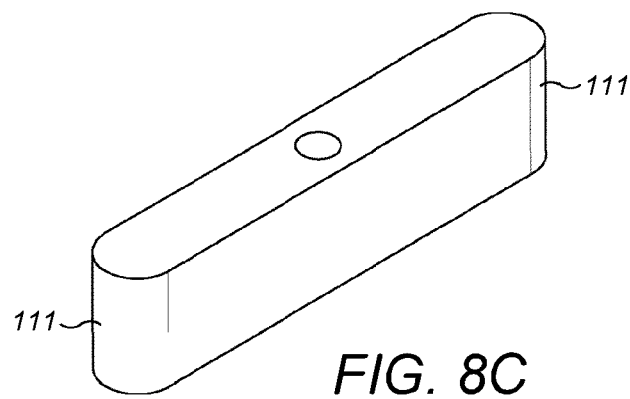

Regarding the cross-sectional shape of the first housing part portion 112 which drives the deformation, shapes with the same circumferential length as the flexible counting ring 130 can be chosen such that they define the position of all points on the counting ring by fitting tightly within it. Alternatively, shapes can be chosen which have a circumferential length which is smaller than the length of the counting ring 130. For example the cross-sectional shape shown in FIG. 8B may be used to drive a counting ring which fits tightly around it or the cross-sectional shape of FIG. 8C may be used to drive the same length counting ring which would leave portion of the counting ring undefined on each of the elongate sides, due the smaller circumference. There is no danger of clashes between the "loose" portions of the counting ring 130 and the teeth of the second housing part because the flexible counting ring 130 cannot support the compressive loads required to create a jam, provided teeth are meshed properly at each of the contact points.

Figure 8D:
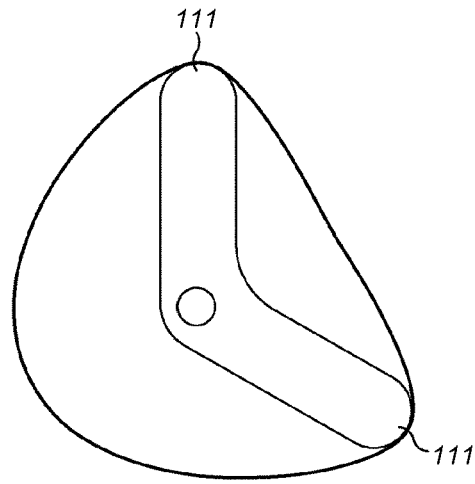
Figure 8E:
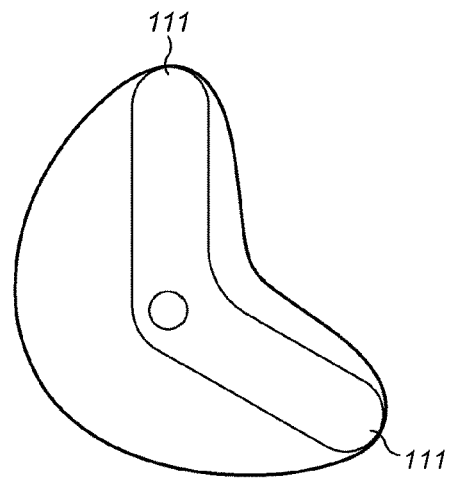

Shapes which have a perimeter length less than that of the counting ring such that they do not fully define the counting ring's position can have multiple different arrangements, depending on the lengths of the counting ring portion between any two adjacent contact points. The gearing down ratio is defined by the number of teeth on the counting ring and therefore (for a given tooth pitch) the total length of the counting ring used. In this way, assuming the counting rings of FIGS. 8D and 8E have the same pitch of teeth and both have less teeth than the second housing part 120, the counting ring of FIG. 8D would provide the greatest gearing down ratio due to its longer length (closer to that of the internal surface of the second housing part 120).

Figure 8F:
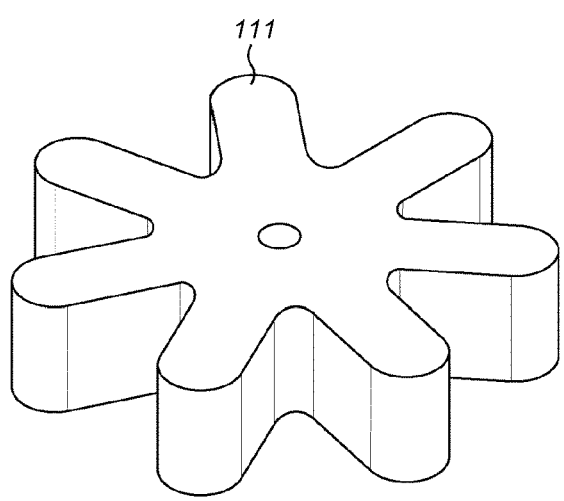

The number of separate regions 141 in phase is equal to the minimum difference in the number of teeth between the two parts. For a fully defined flexible counting ring, the difference in the number of teeth 132 must be a multiple of the number of regions 141 in phase. Because of this, it may be advantageous to use a first housing part 110 with more than two contact points, particularly if the number of contact points required is a prime number such as the first housing part of FIG. 8F which has a cross-sectional shape defining seven protrusions 111.

It is also possible for the shape of the first housing part to provide "virtual" contact points. The shape of FIGS. 8D and 8E for example only has two physical protrusions 111 offset from each other by 120 degrees. However this shape is equivalent to a shape with three protrusions arranged at 120 degree intervals and therefore has a third, "virtual" in phase contact point. Therefore, for a fully defined case, the minimum difference in the number of teeth between the two parts is three since the virtual in phase contact point is included in the total number.

Harmonic Face Gear Mechanism

Figure 9A:
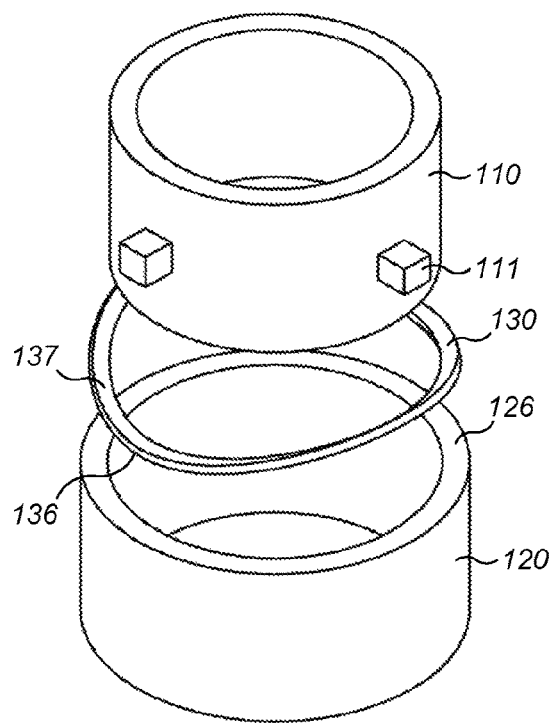
FIGS. 9A and 9B schematically illustrate an exploded and assembled view of a fifth example of a counting mechanism according to the present invention.
Figure 9B:
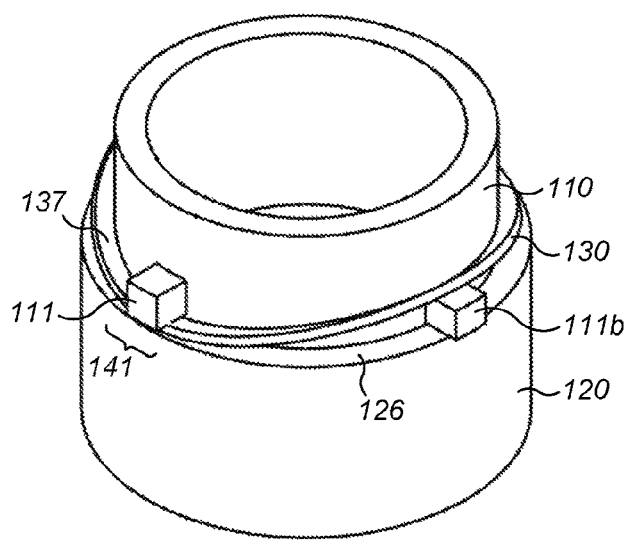

FIGS. 9A and 9B illustrate a further example of a counting mechanism according to the present invention. This mechanism functions similarly to the harmonic gear mechanism but in this example the contacting plane between the counting ring 130 and second housing part 120 is parallel to the direction of rotation of the housing parts 110, 120. As shown in FIG. 9A, an axial facing end face 136 of the counting ring 130 contacts an axial end face 126 of the second housing part and is held in place by protrusions 111 on the first housing part 110.

As with the harmonic mechanism, in this example the counting ring 130 is flexible and can be deformed by contact with the protrusions 111 of the first housing part 110. As with the previously described examples, the first and second housing parts are substantially cylindrical with the diameters sized such that the first housing part 110 lies partially within the second housing part 120 when the mechanism is assembled, as illustrated in FIG. 9B. The diameter of the counting ring 130 is larger than that of the first housing part 110. One or more protrusions extend radially from the first housing part and an axial facing end of the one or more protrusions contacts an axial face 137 of the counting ring, holding a corresponding portion 141 of the lower axial end face 136 of the counting ring 130 in contact with an opposing axial end face 126 of the second housing part 120. The protrusion 111 acts to deform the counting ring, bending the contacted portion 141 out of the plane of the ring to contact the opposing face 126 of the second housing part 120.

Rotation of the housing parts 110 and 120 therefore cause the protrusion 111 to slide against the upper axial end face 137 of the counting ring, causing the deformation of the counting ring to propagate circumferentially around counting ring 130 such that it rolls against the opposing end face 126 of the second housing part 120. Since the counting ring 130 has a larger circumference than that of the second housing part, a full clockwise rotation of the first housing part 110 shown in FIG. 9B, will cause an incremental clockwise rotational displacement of the counting ring 130 with respect to the second housing part. The number of incremental displacements from a known starting point therefore provides a record of the number of rotations of the housing parts as with the other examples of the present invention.

The first housing part 110 may include further protrusions 111b which ensure that other parts of the counting ring 130 remain separated from the second housing part 120. As shown in FIG. 9B, a series of protrusions 111, 111*b* may be provided with the counting ring passing below certain protrusions 111 and above others 111*b*. In this way, the protrusions define the height of the counting ring at certain points, ensuring the counting ring only contacts the second housing parts at the required point. Although in the example of FIG. 9, this function has been performed by a series of protrusions which define the heights of the ring at certain points, it could also be performed by a combination of protrusions (which define heights) and an outer cage which defines a radius which is smaller than the radius of the ring, causing it to deform.

However deformation is achieved, the first housing portion causes the counting ring 130 to deform out of the contacting plane in such a way that it matches the radius of the slightly smaller second housing part 120. As with previous examples opposing arrays of teeth may be provided on the opposing faces of the counting ring and second housing parts such that the teeth mesh at the contacted portion (in-phase) and are in clearance at other points (anti-phase). The rolling motion is then facilitated by a sequential interlocking of teeth around the circumference of the parts.

Further Alternatives

In the above embodiments the first 110 and second 120 housing parts are arranged coaxially such that they may be rotated relative to each other about a mutual axis of rotation. However this does not have to be the case and in some devices it can be advantageous to have a non-coaxial counter, such as if the geometric constraints imposed by the rest of the device mean that this can be more compact than the equivalent coaxial counter.

Figure 10A:
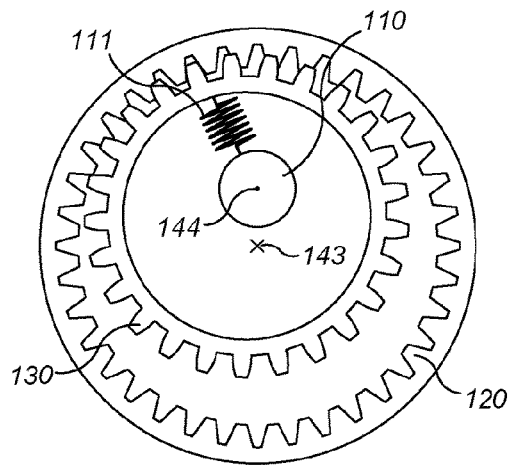
FIGS. 10A to 10F schematically illustrate various alternatives for the constituent parts of the examples of the present invention.
Figure 10B:
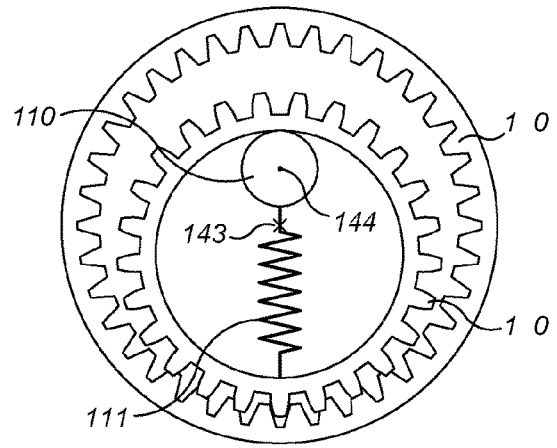

A non-coaxial counter cannot have a rigid radial protrusion 111, because otherwise there are points of the rotation where the radial protrusion is either too small to force contact between the counting ring 130 the second housing part 120, or where it is too large and will cause jams. However, by using a compliant radial protrusion—for example a spring—the protrusion 111 can adjust length to ensure that contact always takes place. FIGS. 10A and 10B schematically illustrate the operation of a mechanism which employs a sprung radial protrusion 111 to drive the counting ring 130 in a non-coaxial arrangement of housing parts 110, 120. FIGS. 10A and 10B shows that the rotational axis 143 of the second housing part 120 is offset from the rotational axis 144 of the first housing part 110. This accounted for by the compliant, sprung protrusion 111 which is chosen so that it can apply a sufficient force to hold the counting ring 130 against the second housing part 120 both on the side closest the axis 144 of the first housing part and the side furthest away from the axis 144 of the first housing part—as illustrated respectively in FIGS. 10A and 10B.

Figure 10C:
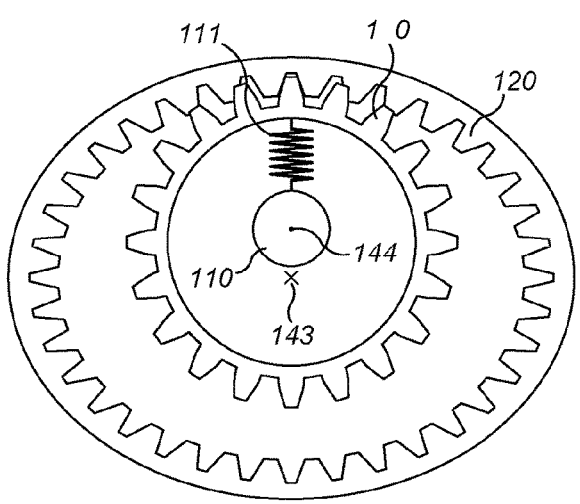

Similarly, although in the examples described above the housing parts are substantially cylindrical with a circular cross-section, other cross-sectional shapes can be used, particularly where the geometry of the rest of the device dictates that such shapes are more efficient than circles. FIG. 10C illustrates a mechanism with a second housing part 120 having an elliptical cross-section. Here again a compliant protrusion 111 may be employed to account for the fact that the radius of the second housing part 120 varies so the protrusion must be able to apply a sufficient force to hold the counting ring 130 in contact with the second housing part 120 for the complete rotation. Again, in the case of FIG. 10C a spring is used for the protrusion 111 which compresses when sliding against the inside of the counting ring 130 past the minor axis of the ellipse and extends when rotating past the major axis of the ellipse. In the latter case, although the force applied by the spring 111 is reduced it is still sufficient to hold the counting ring 130 against the second housing part 120 and provide the rolling contact.

Figure 10D:
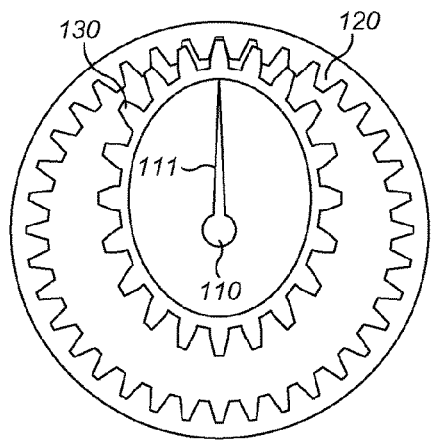

Similarly the counting ring 130 does not need to be circular and the protrusion 111 driving it can take any shape, provided the shapes of the parts are such that the counting ring is held in rolling contact with the second housing part around the full circumference of the second housing part 120. An example is provided in FIG. 10D of an elliptical counting ring 130 being driven by an elongate protrusion 111, which satisfies this condition.

Figure 10E:
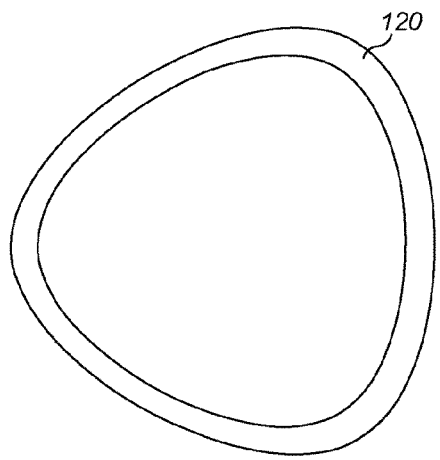
Figure 10F:
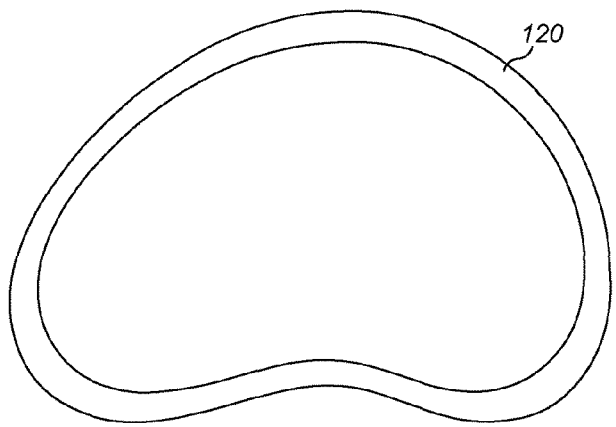

In general, the counting ring 130 and the second housing part 120 can take any smoothly curved shape, provided that the radius of curvature everywhere on the outer gear (for example the second housing part 120 in the examples of FIGS. 1 to 4 or the counting ring 130 in the example of FIG. 6) is larger than the radius of curvature everywhere on the inner gear (the counting ring 130 in the examples of FIGS. 1 to 4 or the second housing part 120 in the example of FIG. 6 for example)—ignoring small bumps, regions which do not mesh and the gear tooth profiles themselves. FIGS. 10E and 10F illustrate examples of the cross-sectional shape of the second housing part 120 which could satisfy this requirement. If the counting ring and second part are provided with arrays of teeth to provide the non-slip condition, the teeth must be the correct size and pitch to fit with the smaller gear having space to roll around the inside of the larger.

The requirement to minimise the maximum radius of curvature for the inner gear means that a circle is the most preferable shape for an inner gear, since this has the same radius of curvature at all points. So for a given size, a circle will always have the smallest maximum radius of curvature. By the same logic a circle is the most preferable shape for an outer gear: it has the same radius of curvature at all points, so for a given size, a circle will always have the largest minimum radius of curvature. Together, these statements mean that the greatest range of potential gearing ratios are achieved by using circles.

Lock Out Mechanism

As described above, the counting mechanism according to the current invention may further comprise a lockout mechanism configured to lock the device at the end of its lifetime.

Generally speaking, the lock out mechanism according to the present invention may be employed in any counting device which comprises: a first housing part 210; a second housing part 220 rotatable with respect to the first housing part 210; and a rotatable counting part 230; wherein rotation of the counting part 230 is driven by rotation of the second housing part 220 such that a full rotation of the second housing 220 part produces an incremental rotation of the counting part 230 with respect to the first housing part 210. FIGS. 11A to 11D schematically illustrate this general structure which is used by the various examples of counting device according to the present invention described above. In FIG. 11 the first housing part 210 is rotatable relative to the second housing part 220 and a full rotation of these housing parts produces an incremental rotational displacement between the rotatable counting part 230 and the second housing part 220.

The mechanism by which the incremental rotation of the counting part 230 is driven by rotation of the first housing part 210 may be by means of a radial protrusion driving a rolling motion of the counting part 230 against the second housing part 220, as is described in the above examples. However it may equally be by any other mechanism which produces an incremental rotation in the counting ring 230 (relative to the second housing part 220) for every rotation of the first housing part 210 (relative to the second housing part 220). For example conventional known gearing systems may equally be used to provide the reduction ratio between the rotations of these respective parts.

Each of the first housing part 210, second housing part 220 and counting part 230 has a locking feature 211, 221, 231 positioned on the part so that it rotates with the part. Considering the second housing part 220 as a fixed reference, the locking feature 211 of the first housing part 210 rotates past the locking feature 221 of the second housing part once every rotation of the first housing part 210 and the locking feature 231 of the counting part 230 rotates past the locking feature 221 of the second housing part once every rotation of the counting part 230.

Figure 11A:
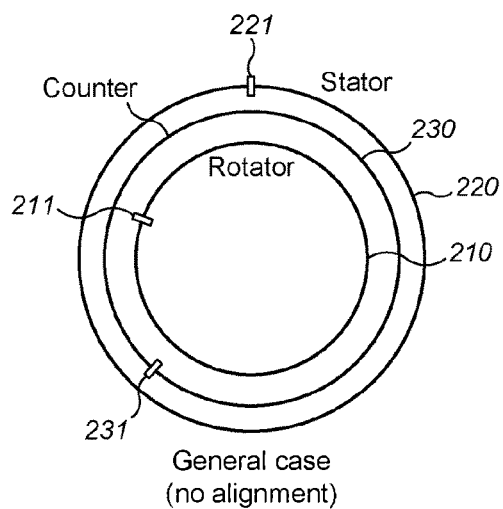
FIGS. 11A to 11D schematically illustrate the principle of operation of the lockout mechanism for a counting mechanism according to the present invention.
Figure 11B:
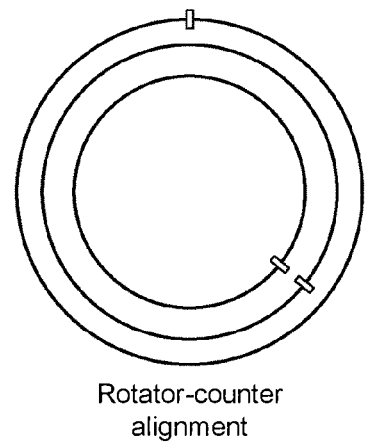
Figure 11C:
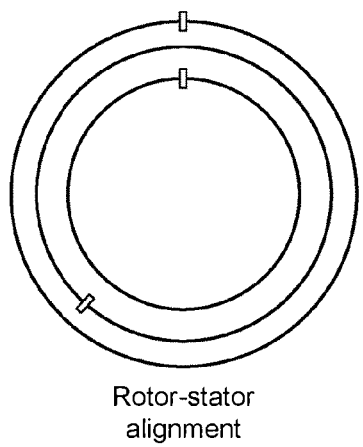
Figure 11D:
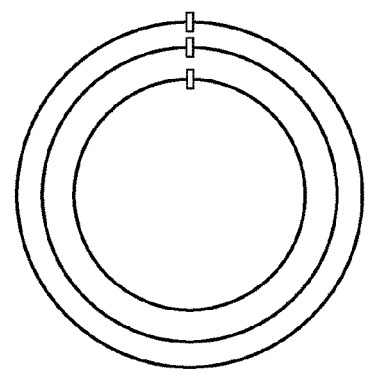

The locking features 211, 221, 231 are configured to engage and lock together only when they are all simultaneously aligned as shown in FIG. 11D. The use of the term "aligned" does not imply adjacency, just that all three of the features are in the unique position in which they interact to lock-out. The locking together of the features prevents the further rotation of the housing parts. The first housing part 210 rotates multiple times (n times) over the lifetime of the device whereas the counting part 230 rotates only once. Of the three possible pairs of these parts, the first housing/counting part locking features and the first/second housing part locking features align multiple times throughout the life of the counter (n−1 and n, respectively), as shown in FIGS. 11B and 11C. The lockout must not trigger in these cases but only when all three of the parts are aligned as shown in FIG. 11D.

The relative position of features 231 and 221 determines how many counts until the device locks out. The relative position of features 211 and 221 determines at what point within the final revolution locking out occurs and can therefore be used to specify the most logical position for a lock out within a final dose. For a device with multiple doses in a single revolution, there can be multiple 211 features, each corresponding to a single dose. The advantage of only having a single 211 feature is that this decreases the tolerance sensitivity on feature 231.

Figure 12A:
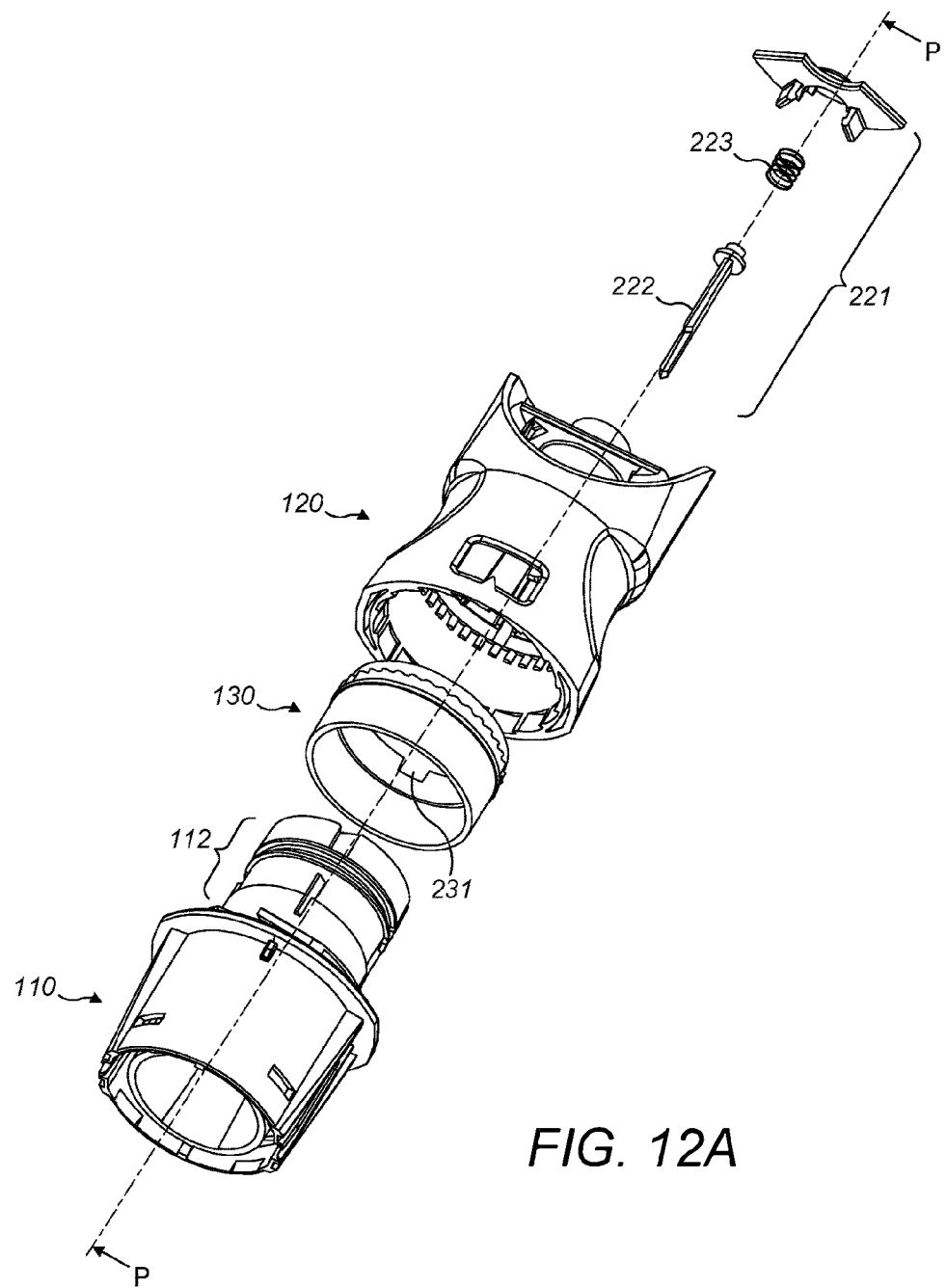
FIG. 12A to 12C schematically illustrate an example of a lockout mechanism employed in a first example of the counting mechanism according to the present invention.
Figure 12B:
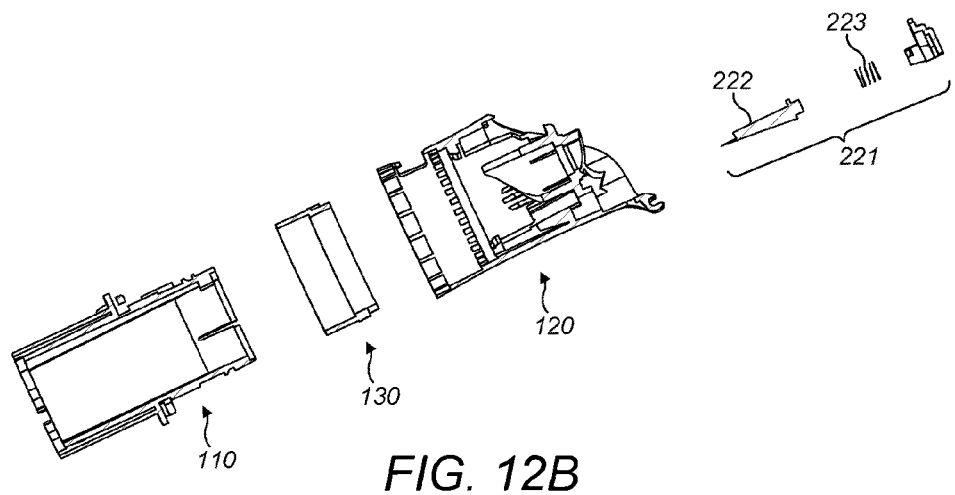
Figure 12C:
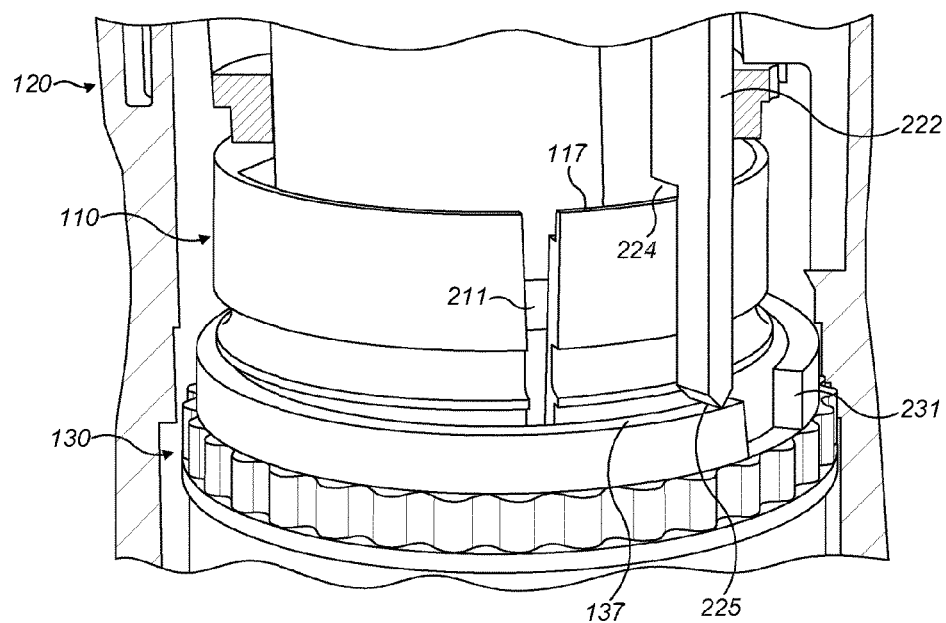

The locking features 211, 221, 231 may take any form appropriate to provide the required locking of the first housing part, second housing part and counting part upon simultaneous alignment of the features. FIGS. 12A to 12C schematically illustrate one example of the lock out mechanism, as employed in the counting mechanism according to the present invention, described above with reference to FIGS. 1 to 4. In this example the locking feature 221 provided on the second housing part comprises a sprung member formed by a rod 222 and spring 223. The rod 222 lies along the elongate axis P-P of the mechanism and is held under the elastic tension of the spring 223 which is biased so as to apply a force to the rod 222 along the axis P-P towards the first housing part 110.

The locking features of the first housing part 110 and counting part 130 each comprise an axially directed slot which are both shaped so as to receive the rod 222. As shown in FIG. 12C, the end of the rod 222 has a stepped-shape and is staggered in length such that a first end face 224 contacts the axial end face 117 of the first housing part portion 112 and a longer section has an end face 225 which contacts an axial end face 137 of the counting ring. Since the counting ring 130 has a greater diameter than the first housing part portion 112, when assembled the counting ring axial end face 137 extends radially beyond the axial end face 117 of the first housing part 110. The two offset end faces 117, 137 of the first housing part 110 and the counting ring 130 therefore meet the staggered end faces of the rod and prevent the movement of the rod, holding it in a primed position under the tension of the spring 223.

As described above, the first housing part 110 rotates many times during the life time of the device such that the locking feature slot 211 of the first housing part will rotate under the rod 222. However since the rod 222 remains supported at its end face 225 by the top axial end face 137 of the counting ring 130, the rod 222 is not permitted to move into the slot 211 under the action of the spring 223. It is only after a sufficient number of rotations of the housing parts 110, 120 to drive the counting ring 130 through sufficient incremental rotations to align both slots 211, 231 under the rod 222, that the rod is driven into both slots 211, 231 under the action of the spring to trigger the lockout.

The sprung member is driven into the slots orthogonally to the direction of rotation of the housings. This effectively locks the first housing, second housing and counting ring together which, when applied in a dispenser, prevents the user from dispensing more doses. For example, the mechanism may have an end of life lockout which triggers after 70 doses. In this case the slots only align once 70 doses have been dispensed.

Although in the above example the locking features are provided by a sprung feature and two slots, the slots can equally be replaced with raised posts. Furthermore the locking features may take any other form suitable to lock the three rotatable parts together upon simultaneous alignment of the features.

The counting mechanism according to the present invention has a number of advantages. Firstly the mechanism provides a large reduction ratio between a rotation of housing parts to a incremental rotational displacement of a counting ring such that a record of a large number of rotations can be kept. Importantly, the arrangement of the mechanism allows this to be achieved in a compact form. Since the movement of the counting part is via rolling movement, the mechanism has greatly reduced wear and therefore an improved lifetime and resistance to failure of the parts. This allows means that the device operates with very little noise.

The counting mechanism according to the present invention only requires three parts and therefore is low cost and easy to manufacture and assemble. In particular the number of part changes between devices with different counts can be minimised through design. For instance, when designing a device with both a 35:1 to and a 70:1 counting variant, the 35:1 dose counter could be designed to have 72 teeth on the upper housing and 70 on the counting ring and the 70:1 dose counter could be designed to have 71 teeth on the upper housing and 70 on the counting ring. This way, the moulding for the counting ring does not have to change between variants.

Due to the mechanical advantage provided by the system, any friction within the counting mechanism is easily overcome by the user and transmitted forces are low so the parts can be cheaply moulded out of plastic. All parts can be moulded with a single line of draw and part assembly is largely axisymmetric. Since the counter is held in place by the upper and lower housing it does not require additional retaining features. The perimeter of the counting ring has more space available than the corresponding linear distance, so there is more room to indicate each increment. It is also easy to design a new counter with a different gearing ratio, simply by a change in the number of teeth.

The mechanism according to the present invention is furthermore highly accurate and has very little backlash. The counting mechanism is also resilient to shocks, particularly when teeth are included in the device, since some teeth are always meshed. It is also advantageous that the parts may have integrally formed teeth on their outside or inside surfaces since there is no cost to forming these teeth as they may be formed when the parts are being cored out.

The lock-out mechanism according to the present invention provides a simple means to prevent a three part rotatable counting mechanism from continued rotation after a predetermined number of rotations of the constituent housing parts. Since the rotation of the counting mechanism is geared down from the rotation of the housing parts, the three parts only align once during the lifetime of the device and this may be used to initialise lockout. The simplicity of the mechanism means it is straightforward and low cost to manufacture and the possibility of failure is reduced. The possibility of introducing a sprung feature which is driven orthogonally to the direction of rotation means the parts are tightly locked and cannot be easily overcome by applying a force to rotate the housing parts.

The invention claimed is:

1. An inhaler device for dispensing multiple doses, the inhaler device comprising:
   a first housing part;
   a second housing part rotatable with respect to the first housing part;
   a first lock provided on the first housing part,
   a second lock provided on the second housing part, and
   a rotatable first counting part including a third lock provided on the first counting part,
   wherein the first lock, the second lock, and the third lock are configured to lock together when all are simultaneously aligned;
   wherein after a predetermined number of rotations of the second housing part with respect to the first housing part, the first lock, the second lock, and the third lock are driven into alignment to prevent further rotation of the second housing part with respect to the first housing part.

2. The inhaler device of claim 1, wherein the second lock of the second housing part is configured to align with the first lock of the first housing part once every full rotation of the second housing part with respect to the first housing part and the third lock of the first counting part is configured to align with the first lock of the first housing part once every full rotation of the first counting part with respect to the first housing part.

3. The inhaler device of claim 1, wherein the first lock of the first housing part and the second lock of the second housing part align multiple times before all the first lock, the second lock, and the third lock align to prevent further rotation of the second housing part with respect to the first housing part.

4. The inhaler device of claim 1, wherein one of the first lock, the second lock, and the third lock comprises a sprung member and the other two of the first lock, the second lock, and the third lock each comprise a slot; wherein
   the slots and sprung member align after a predefined number of rotations upon which the sprung member is driven into the slots orthogonally to the direction of rotation, locking the first housing part, the second housing part, and the first counting part together.

5. The inhaler device of claim 1, wherein the first housing part and the second housing part are coaxial.

6. The inhaler device of claim 1, wherein the second housing part is cylindrical.

7. The inhaler device of claim 1, wherein
   a predefined rotation of the first housing part and the second housing part is associated with a dispensing function, such that the rotational displacement of the first counting part and the second housing part provides a record of the number of doses dispensed.

8. The inhaler device of claim 1 further comprising:
   a ratchet provided on one of the first housing part or the second housing part; and
   a pawl provided on the other of the first housing part and the second housing part; such that only one direction of relative rotation is permitted by the first housing part and the second housing part.

9. The inhaler device of claim 1, wherein at least one of the first lock, the second lock, or the third lock comprises a sprung member, which is triggered upon simultaneous alignment with the other two of the first lock, the second lock, and the third lock.

10. The inhaler device of claim 9, wherein the sprung member is driven orthogonally to the direction of rotation of the first housing part and the second housing part.

11. The inhaler device of claim 1, wherein:
    the second housing part has a curved cross-sectional shape;
    the first counting part comprises a counting ring disposed between the first housing part and the second housing part;
    the first housing part comprises a protrusion which abuts the counting ring, holding a portion of the counting ring in contact with the second housing part; wherein
    relative rotation of the first housing part and the second housing part causes the protrusion to slide against a surface of the counting ring to drive a rolling movement of the counting ring around the circumference of the second housing part; such that
    a predefined rotation of the first housing part and the second housing part produces an incremental rotational displacement between the counting ring and the second housing part to record a count.

12. The inhaler device of claim 11, wherein:
    the first housing part has multiple protrusions;
    the counting ring is flexible such that the protrusions abut the counting ring causing it to deform and contact the second housing part at positions corresponding to the protrusions; and
    relative rotation of the first housing part and the second housing part causes the deformation of the counting ring to propagate around its circumference, driving a sequential interlocking of teeth at the contact portions of the counting ring and second housing part; wherein
    the incremental rotational displacement between the counting ring and second housing part is provided by the difference in number of teeth.

13. The inhaler device of claim 11, wherein
    opposing surfaces of the counting ring and the second housing part are high friction surfaces such that they produce a non-slip contact; wherein
    relative rotation of the first housing part and the second housing part causes the protrusion to drive a rolling, non-slip movement of the counting ring against the second housing part; and
    a difference in a circumference of the counting ring and contacting surface of the second housing part produces the incremental rotational displacement between the counting ring and the second housing part.

14. The inhaler device of claim 1, wherein the first counting part comprises a counting ring disposed between the first housing part and the second housing part, the inhaler device further comprising:
- a first array of gear teeth provided around a circumference of the counting ring and a second array of gear teeth provided around a circumference of the second housing part, the first array of gear teeth and the second array of gear teeth positioned on opposing surfaces, the number of teeth in the first array on the counting ring differing from the number of teeth in the second array on the second housing part; wherein
- the first housing part comprises a protrusion which abuts the counting ring, holding a portion of the counting ring in contact with the second housing part such that the opposing teeth of the counting ring and the second housing part mesh at the contacted portion; and
- relative rotation of the first housing part and the second housing part causes the protrusion to slide against a surface of the counting ring to drive a rolling movement of the counting ring around the circumference of the second housing part, the rolling movement of the counting ring against the second housing part comprising a sequential interlocking of teeth of the counting ring with those of the second housing part; such that a predefined rotation of the first housing part and second housing part produces an incremental rotational displacement between the counting ring and the second housing part due to the difference in number of teeth in the first array and second array.

15. The inhaler device of claim 14, wherein:
- the first housing part is positioned at least partially within the second housing part, the counting ring disposed around the first housing part;
- the first array of teeth is provided on an inner surface of the second housing part;
- the second array of teeth is provided on an outer surface of the counting ring, the counting ring having less teeth than the second housing part; and
- the protrusion extends radially from an outer surface of the first housing part, the protrusion abutting an inner surface of the counting ring, displacing the counting ring off-axis to contact the second housing part; such that
- relative rotation of the first housing part and the second housing part causes the protrusion to drive an eccentric rotation of the counting ring about an axis of the second housing part.

16. The inhaler device of claim 14, wherein
- the second housing part is positioned at least partially within the first housing part, the counting ring disposed around the second housing part;
- the first array of teeth is provided on an outer surface of the second housing part;
- the opposing array of teeth is provided on an inner surface of the counting ring, the counting ring having more teeth than the second housing part; and
- the protrusion extends radially from an inner surface of the first housing part, the protrusion abutting an outer surface of the counting ring, displacing the counting ring off-axis to contact the second housing part; such that
- relative rotation of the first housing part and the second housing part causes the protrusion to drive an eccentric rotation of the counting ring about an axis of the second housing part.

17. The inhaler device of claim 1, wherein rotation of the first counting part is driven by rotation of the second housing part such that a full rotation of the second housing part produces an incremental rotation of the first counting part with respect to the first housing part to record a count.

18. The inhaler device of claim 17, wherein a gearing ratio between a predefined rotation of the first housing part and the second housing part and incremental rotational displacement of a counting ring and second housing part is between 3:1 and 300:1.

19. The inhaler device of claim 17, further comprising:
- a second counting part coupled with the first counting part, such that every complete rotation of the first counting part relative to the second housing part produces an incremental rotational displacement between the second counting part and the second housing part.

20. The inhaler device of claim 17, wherein the first housing part and the second housing part are coaxial.

* * * * *